(12) United States Patent
Carnahan et al.

(10) Patent No.: US 8,410,189 B2
(45) Date of Patent: Apr. 2, 2013

(54) CROSSLINKED POLYALKYLENEIMINE HYDROGELS WITH TUNABLE DEGRADATION RATES

(75) Inventors: Michael A. Carnahan, Durham, NC (US); Jared D. G. Butlin, Durham, NC (US)

(73) Assignee: HyperBranch Medical Technology, Inc., Durham, NC (US)

( * ) Notice: Subject to any disclaimer, the term of this patent is extended or adjusted under 35 U.S.C. 154(b) by 111 days.

(21) Appl. No.: 12/371,113

(22) Filed: Feb. 13, 2009

(65) Prior Publication Data

US 2009/0215923 A1    Aug. 27, 2009

Related U.S. Application Data

(60) Provisional application No. 61/028,288, filed on Feb. 13, 2008.

(51) Int. Cl.
*A61K 8/72* (2006.01)
*A61L 24/00* (2006.01)

(52) U.S. Cl. ............... 523/105; 523/113; 523/118

(58) Field of Classification Search ............ 523/118
See application file for complete search history.

(56) References Cited

U.S. PATENT DOCUMENTS

| | | | |
|---|---|---|---|
| 4,920,158 A | 4/1990 | Murray et al. | |
| 5,122,614 A | 6/1992 | Zalipsky | |
| 5,143,071 A | 9/1992 | Keusch et al. | |
| 5,328,955 A * | 7/1994 | Rhee et al. | 525/54.1 |
| 5,672,638 A | 9/1997 | Verhoeven | |
| 5,936,035 A * | 8/1999 | Rhee et al. | 525/54.1 |
| 6,258,351 B1 | 7/2001 | Harris | |
| 6,348,558 B1 | 2/2002 | Harris et al. | |
| 6,362,276 B1 | 3/2002 | Harris et al. | |
| 6,531,147 B2 | 3/2003 | Sawhney et al. | |
| 6,558,658 B2 | 5/2003 | Harris | |
| 6,818,018 B1 | 11/2004 | Sawhney | |
| 7,018,624 B2 | 3/2006 | Harris et al. | |
| 7,053,150 B2 | 5/2006 | Kozlowski et al. | |
| 7,074,878 B1 | 7/2006 | Harris et al. | |
| 7,259,224 B2 | 8/2007 | Harris et al. | |
| 2001/0016624 A1 | 8/2001 | Harris et al. | |
| 2002/0064546 A1 | 5/2002 | Harris | |
| 2003/0202955 A1 | 10/2003 | Harris | |
| 2003/0232746 A1 | 12/2003 | Lamberti et al. | |
| 2004/0023842 A1 * | 2/2004 | Pathak et al. | 514/1 |
| 2004/0147466 A1 * | 7/2004 | Barman et al. | 514/44 |

(Continued)

OTHER PUBLICATIONS

Ahn et al, 2002, "Biodegradable poly(ethylenimine) for plasmid DNA delvery", Journal of Controlled Release, vol. 80, p. 273-282.*

(Continued)

*Primary Examiner* — Peter F Godenschwager
*Assistant Examiner* — David Karst
(74) *Attorney, Agent, or Firm* — Alan W. Steele; Foley Hoag LLP

(57) ABSTRACT

One aspect of the present invention relates to methods of sealing a wound or tissue plane or filling a void space, or securing meshes, films or other devices within the body. In certain embodiments, the wound is an ophthalmic, pleural or dural wound, or a hernia repair mesh. Remarkably, disclosed herein is the discovery that the use of certain crosslinkers in combination with polyalkyleneimines at specific concentrations can result in hydrogels with tunable degradation properties.

22 Claims, 20 Drawing Sheets

| Polyethylene glycol derivative | Crosslinking Agent | |
|---|---|---|
| PEG$_{3350}$-(succinimidyl succinate)$_2$ | PEI$_{2000}$ | Lys-Lys-Lys |
| PEG$_{3350}$-(succinimidyl glutarate)$_2$ | PEI$_{2000}$ | Lys-Lys-Lys |
| PEG$_{3350}$-(succinimidyl adipate)$_2$ | PEI$_{2000}$ | Lys-Lys-Lys |
| PEG$_{3350}$-(succinimidyl sebacate)$_2$ | PEI$_{2000}$ | Lys-Lys-Lys |

[A]

| Crosslinking Agent | 1° amines | 2° amines | 3° amines |
|---|---|---|---|
| PEI$_{25000}$ | 18 | 22 | 14 |
| PEI$_{2000}$ | 18 | 17 | 12 |
| PEI$_{800}$ | 18 | 14 | 9 |
| PPI(DAB)-G1 | 18 | 0 | 9 |
| Trilysine | 4 | 0 | 0 |

[B]

U.S. PATENT DOCUMENTS

| | | | |
|---|---|---|---|
| 2005/0266086 A1* | 12/2005 | Sawhney | 424/486 |
| 2006/0134050 A1 | 6/2006 | Griffith et al. | |
| 2006/0239961 A1 | 10/2006 | Bentley et al. | |
| 2006/0247377 A1 | 11/2006 | Riegel et al. | |
| 2007/0128681 A1 | 6/2007 | Barman et al. | |
| 2007/0196454 A1 | 8/2007 | Stockman et al. | |
| 2007/0276116 A1 | 11/2007 | Harris et al. | |
| 2009/0220607 A1 | 9/2009 | Kiser et al. | |

OTHER PUBLICATIONS von Harpe et al., 2000, "Characterization of commercially available and synthesized polyethylenimines for gene delivery", Journal of Controlled Release, vol. 69, p. 309-322.*

International Search Report for PCT/US09/034050 mailed Sep. 14, 2009.

* cited by examiner

| Polyalkylene Glycol | Polyalkyleneimine | Weight % crosslinking components | Ratio PAG:PAI (w/w) | Set Time (Sec) | Time to Dissolution (hr) | Phosphate Conc. (mM) | Borate Conc. (mM) | Carbonate Conc. (mM) |
|---|---|---|---|---|---|---|---|---|
| $PEG_{3350}$-$(SG)_2$ | $PEI_{2000}$ | 15 | 15:01 | 20 | ~96 | 141.4 | 25 | 25 |
| $PEG_{3350}$-S3MG | $PEI_{2000}$ | 15 | 15:01 | 20 | < 24 | 143.1 | 25 | 25 |
| $PEG_{3350}$-S3,3DMG | $PEI_{2000}$ | 15 | 15:01 | 27 | < 24 | 10 | 65 | 25 |

| Polyethylene glycol derivative | Crosslinking Agent | |
|---|---|---|
| $PEG_{3350}$-(succinimidyl succinate)$_2$ | $PEI_{2000}$ | Lys-Lys-Lys |
| $PEG_{3350}$-(succinimidyl glutarate)$_2$ | $PEI_{2000}$ | Lys-Lys-Lys |
| $PEG_{3350}$-(succinimidyl adipate)$_2$ | $PEI_{2000}$ | Lys-Lys-Lys |
| $PEG_{3350}$-(succinimidyl sebacate)$_2$ | $PEI_{2000}$ | Lys-Lys-Lys |

[A]

| Crosslinking Agent | 1° amines | 2° amines | 3° amines |
|---|---|---|---|
| $PEI_{25000}$ | 18 | 22 | 14 |
| $PEI_{2000}$ | 18 | 17 | 12 |
| $PEI_{800}$ | 18 | 14 | 9 |
| PPI(DAB)-G1 | 18 | 0 | 9 |
| Trilysine | 4 | 0 | 0 |

[B]

Figure 3
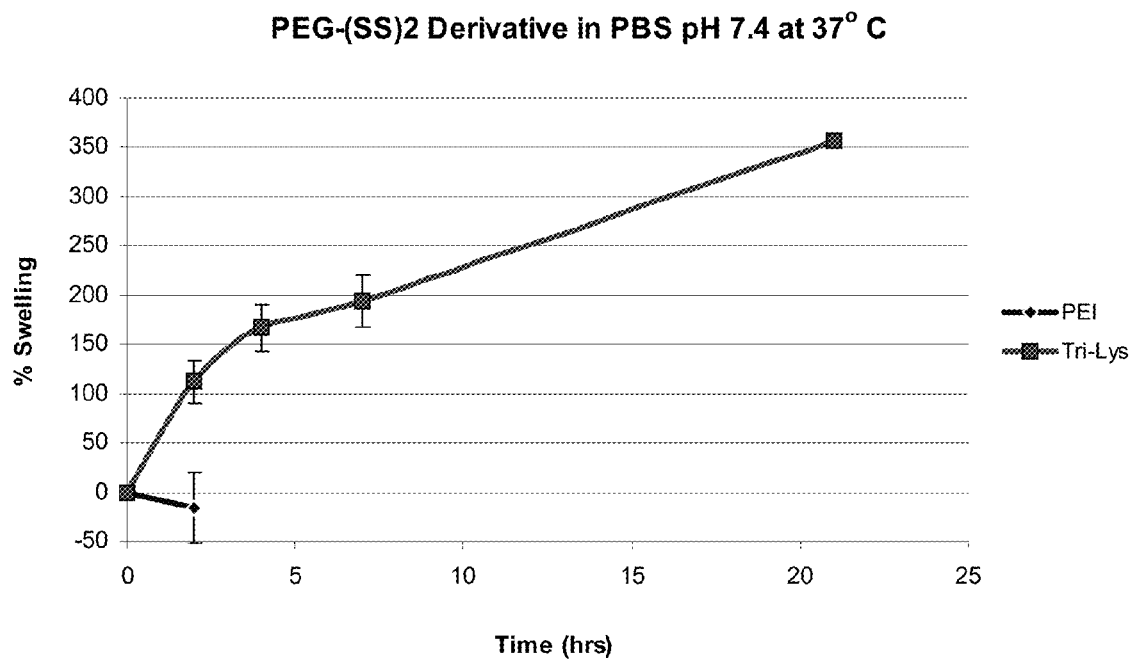
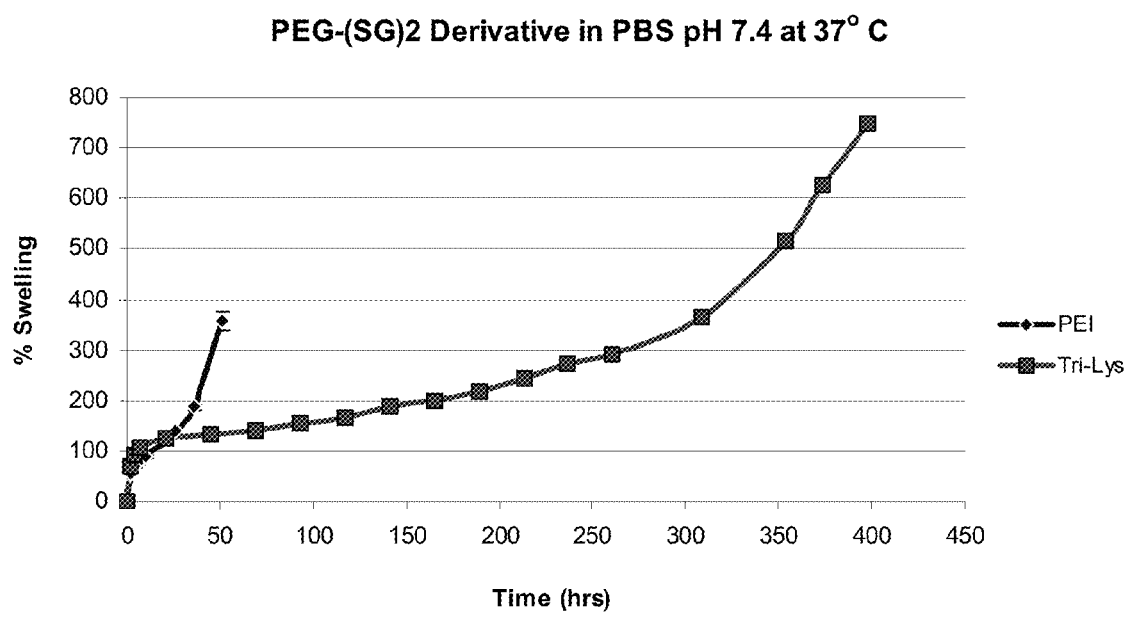

Figure 4
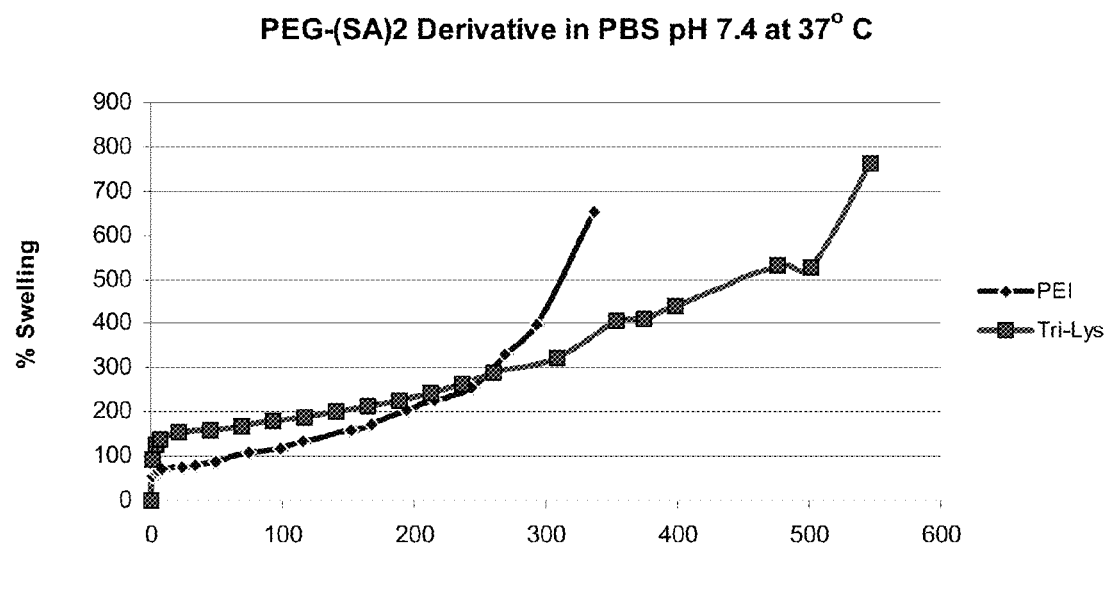
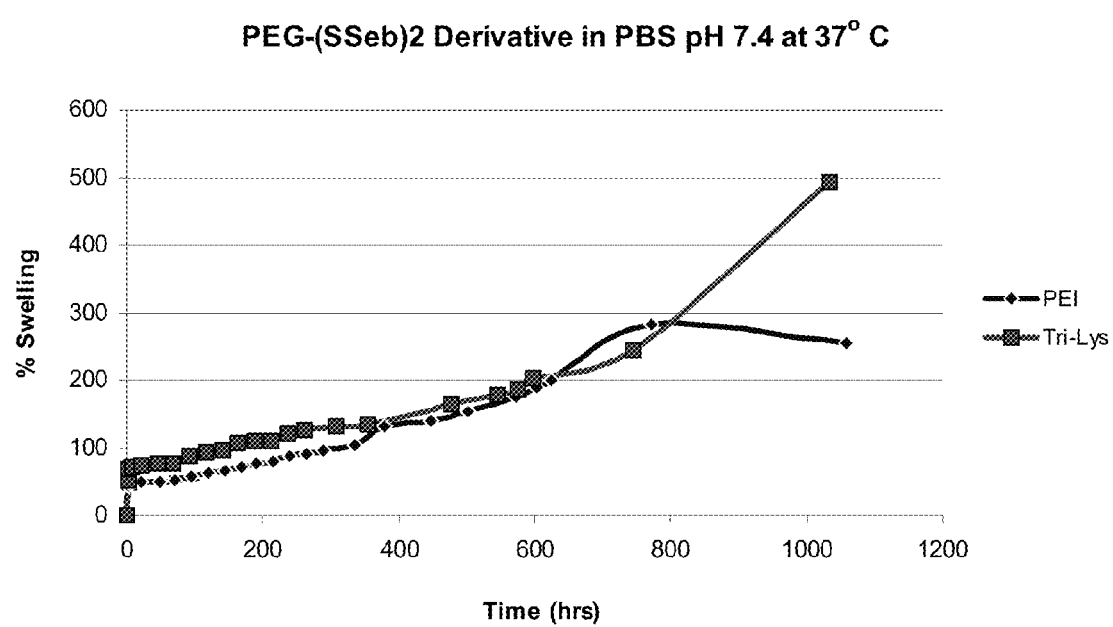

Figure 5
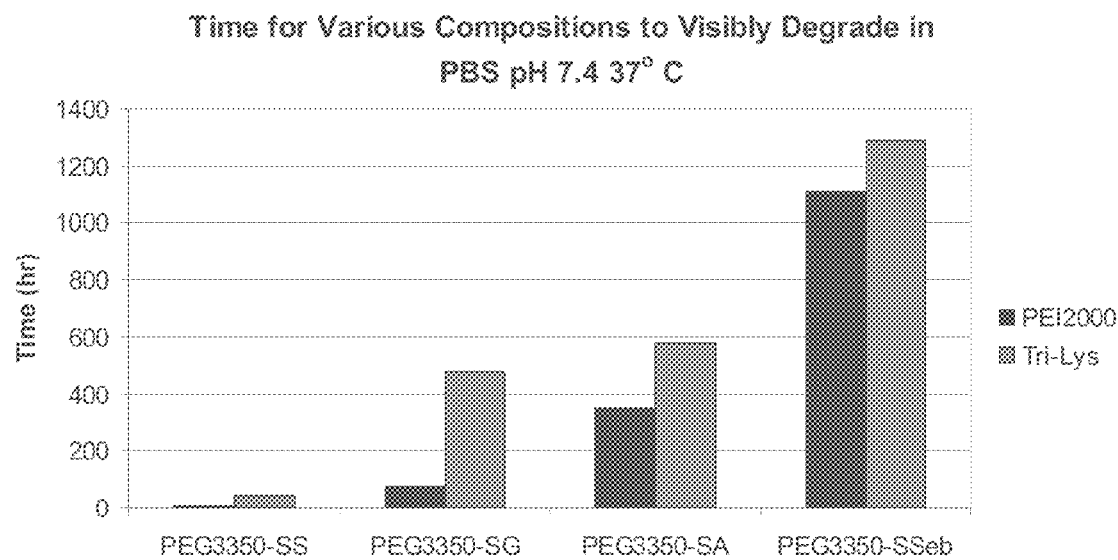
[A]
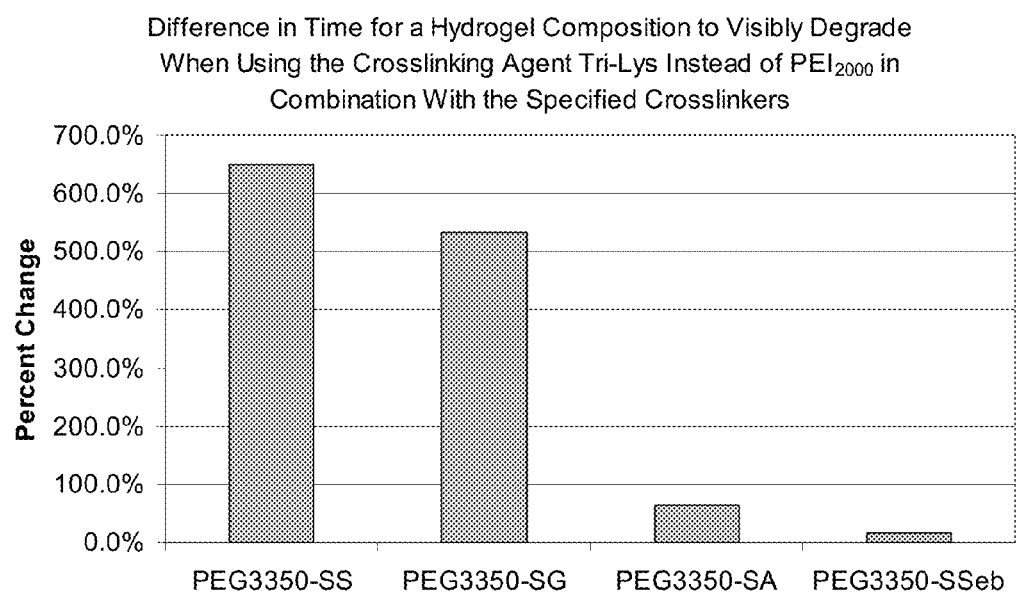
[B]

| Polyalkylene Glycol | Polyalkyleneimine | Weight % crosslinking components | Ratio PAG:PAI (w/w) | Set Time (Sec) | Phosphate Conc. (mM) | Borate Conc. (mM) | % Swelling 24 hr 37 °C |
|---|---|---|---|---|---|---|---|
| PEG$_{3350}$-SSeb | PEI$_{2000}$ | 15 | 8.7:1 | 1-2 | 50.4 | 35.2 | 29 |
| PEG$_{3350}$-SSeb | PEI$_{2000}$ | 15 | 13.0:1 | 1-2 | 50.4 | 35.2 | 39 |
| PEG$_{3350}$-SSeb | PEI$_{2000}$ | 15 | 8.68:1 | 1-2 | 146.1 | 35 | 66 |

[A]

[B]

Figure 7
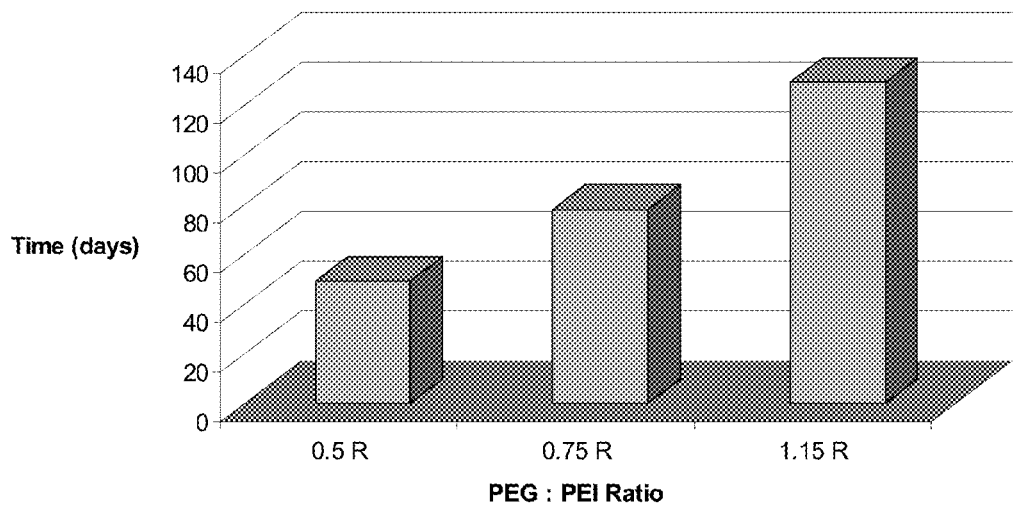
[A]
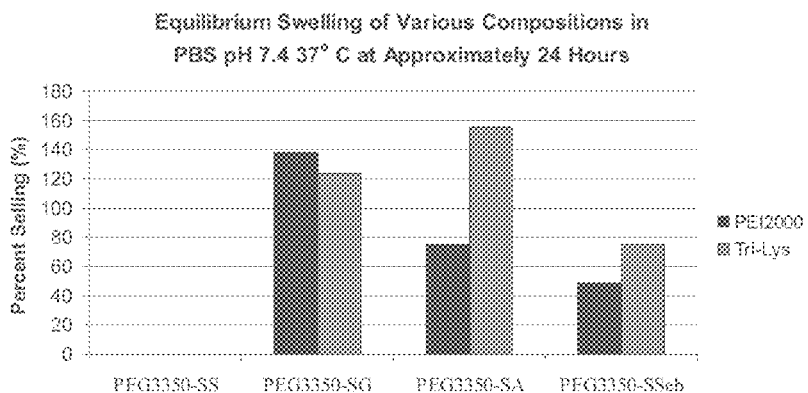
[B]
| Crosslinking Agent | Mw (g/mol) | 1° Amines | 2° Amines | 3° Amines | Swelling at ~40hrs |
|---|---|---|---|---|---|
| PEI$_{2000}$ | 2000 | 17.82 | 16.75 | 11.94 | 135%* |
| PEI$_{1300}$ | 1300 | 11.86 | 10.79 | 7.59 | 168% |
| PPI-DAB (G1) | 316 | 4 | 0 | 2 | 338% |
* calculated value based upon swelling data of 97% at 25hrs, and 211% 70hrs.
[C]

Figure 8

| PEG $M_w$ | Mass of PEG (g) | Desired Difunctional Derivative | Mass of Diacid (g) | Mass of Diacid Anhydride (g) | Mass of N-Hydroxy-succinimide (g) | Mass of DCC (g) |
|---|---|---|---|---|---|---|
| PEG-(OH)$_2$ 3350 | 200 | succinimidyl succinate (SS) | 0.63 | 27.25 | 27.48 | 49.27 |
| PEG-(OH)$_2$ 3350 | 200 | succinimidyl glutarate (SG) | 0.63 | 27.25 | 27.48 | 49.27 |
| PEG-(OH)$_2$ 3350 | 200 | succinimidyl adipate (SA) | 0.63 | 27.25 | 27.48 | 49.27 |
| PEG-(OH)$_2$ 4600 | 48.18 | succinimidyl glutarate (SG) | 0.1642 | 4.82 | 6.60 | 11.83 |
| PEG-(OH)$_2$ 6000 | 65.69 | succinimidyl glutarate (SG) | 0.1298 | 4.93 | 9.21 | 16.51 |
| PEG-(OH)$_2$ 8000 | 68.40 | succinimidyl glutarate (SG) | 0.0932 | 3.18 | 9.40 | 16.50 |
| PEG-(OH)$_2$ 10000 | 200.76 | succinimidyl glutarate (SG) | 0.2243 | 9.18 | 6.02 | 11.5 |
| Pluronic F-127 | 50 | succinimidyl glutarate (SG) | .042 | 2.82 | 1.26 | 3.21 |

[A]

| PEG $M_w$ | Mass of PEG (g) | Desired Difunctional Derivative | Mass of Diacid (g) | Volume Sulfuric Acid (mL) | Mass of N-Hydroxy-succinimide (g) | Mass of DCC (g) |
|---|---|---|---|---|---|---|
| PEG-(OH)$_2$ 3350 | 150 | succinimidyl adipate (SA) | 78.52 | 1.0 | 30.92 | 83.15 |
| PEG-(OH)$_2$ 3350 | 200 | succinimidyl suberate (SSub) | 124.8 | 1.0 | 41.23 | 110.86 |
| PEG-(OH)$_2$ 3350 | 200 | succinimidyl sebacate (SSeb) | 144.9 | 1.0 | 41.23 | 110.86 |
| PEG-(OH)$_2$ 4600 | 150 | succinimidyl adipate (SA) | 57.18 | 1.0 | 22.52 | 60.55 |
| PEG-(OH)$_2$ 4600 | 200 | succinimidyl suberate (SSub) | 90.88 | 1.0 | 30.02 | 80.73 |
| PEG-(OH)$_2$ 4600 | 200 | succinimidyl sebacate (SSeb) | 105.52 | 1.0 | 30.02 | 80.73 |
| PEG-(OH)$_2$ 6000 | 150 | succinimidyl adipate (SA) | 43.84 | 1.0 | 17.26 | 46.42 |
| PEG-(OH)$_2$ 6000 | 200 | succinimidyl suberate (SSub) | 69.68 | 1.0 | 23.01 | 61.89 |
| PEG-(OH)$_2$ 6000 | 200 | succinimidyl sebacate (SSeb) | 80.9 | 1.0 | 23.01 | 61.89 |

| PAG-NHS | PAI or Trilysine | Weight % crosslinking components | Ratio PAG:PAI (w/w) | Swelling @ 24 hr 37 °C (%) Completely | Set Time (Sec) | Phosphate Conc. (mM) | Borate Conc. (mM) |
|---|---|---|---|---|---|---|---|
| PEG$_{3350}$(SS)$_2$ | PEI$_{2000}$ | 15 | 12.5:1 | Degraded | 31 | 195.8 | 25 |
| PEG$_{3350}$(SS)$_2$ | Trilysine | 15 | 14.9:1 | 220 | 24 | 0 | 66.5 |
| PEG$_{3500}$(SG)$_2$ | PEI$_{2000}$ | 15 | 12.6:1 | 88 | 38 | 195.8 | 25 |
| PEG$_{3550}$(SG)$_2$ | Trilysine | 15 | 15:1 | 130 | 19 | 0 | 66.5 |
| PEG$_{3550}$(SA)$_2$ | PEI$_{2000}$ | 15 | 12.8:1 | 72 | 43 | 195.8 | 25 |
| PEG$_{3550}$(SA)$_2$ | Trilysine | 15 | 15.2:1 | 137 | 22 | 0 | 66.5 |
| PEG$_{3550}$(SSeb)$_2$ | PEI$_{2000}$ | 15 | 13:1 | 49 | 87.5 | 195.8 | 25 |
| PEG$_{3550}$(SSeb)$_2$ | Trilysine | 15 | 15.6:1 | 87 | 22 | 0 | 66.5 |

In the chart: Polyethylene Glycol (PEG); Succinimidyl Succinate (SS); Succinimidyl Glutarate (SG); Succinimidyl Adipate (SA); Succinimidyl Sebacate (SSeb); Succinimidyl Propionic Acid (SPA); polyethyleneimine (PEI); Lys-Lys-Lys (Trilysine).

Figure 10

| Inoculum Concentration (CFU/0.1 mL) | | *S. aureus* ATCC 6538 | *K. pneumoniae* ATCC 4352 |
|---|---|---|---|
| | | $2.0 \times 10^5$ | $2.3 \times 10^5$ |
| Formulation 1 | Initial Contact Time (CFU/Sample) | $2.0 \times 10^5$ | $2.3 \times 10^5$ |
| | 24 Hour Contact Time (CFU/Sample) | $2.0 \times 10^5$ | $5.9 \times 10^4$ |
| | Percent Reduction | NR | 74.35% |
| | | | |
| Formulation 3 | Initial Contact Time (CFU/Sample) | $2.0 \times 10^5$ | $2.3 \times 10^5$ |
| | 24 Hour Contact Time (CFU/Sample) | $< 1.0 \times 10^2$ | $3.5 \times 10^2$ |
| | Percent Reduction | > 99.95% | 99.85% |

Figure 11

| Formulation | R value (mass of PEI to complement 1 g of PEG) | Extract pH |
|---|---|---|
| Formulation 1 | 1.15 (50.08 mg) | 7.12 |
| Formulation 2 | 0.75 (76.78 mg) | 7.94 |
| Formulation 3 | 0.50 (115.18 mg) | 8.0 |

Figure 12

| Inoculum Concentration (CFU/0.1 mL) | Staphylococcus aureus ATCC 6538 |
|---|---|
| | $1.5 \times 10^5$ |

| Trial 1 | Initial Contact Time (CFU/Sample) | $1.5 \times 10^5$ |
|---|---|---|
| | 24 Hour Contact Time (CFU/Sample) | $2.3 \times 10^5$ |
| | Percent Reduction | NR |

| Trial 2 | Initial Contact Time (CFU/Sample) | $1.5 \times 10^5$ |
|---|---|---|
| | 24 Hour Contact Time (CFU/Sample) | $2.6 \times 10^5$ |
| | Percent Reduction | NR |

| Trial 3 | Initial Contact Time (CFU/Sample) | $1.5 \times 10^5$ |
|---|---|---|
| | 24 Hour Contact Time (CFU/Sample) | $3.3 \times 10^5$ |
| | Percent Reduction | NR |

Figure 13

| Inoculum Concentration (CFU/0.1 mL) | | *Staphylococcus aureus* ATCC 6538 |
|---|---|---|
| | | $1.5 \times 10^5$ |

| | | |
|---|---|---|
| Trial 1 | Initial Contact Time (CFU/Sample) | $1.5 \times 10^5$ |
| | 24 Hour Contact Time (CFU/Sample) | $< 1.0 \times 10^2$ |
| | Percent Reduction | > 99.93 % |

| | | |
|---|---|---|
| Trial 2 | Initial Contact Time (CFU/Sample) | $1.5 \times 10^5$ |
| | 24 Hour Contact Time (CFU/Sample) | $< 1.0 \times 10^2$ |
| | Percent Reduction | > 99.93 % |

| | | |
|---|---|---|
| Trial 3 | Initial Contact Time (CFU/Sample) | $1.5 \times 10^5$ |
| | 24 Hour Contact Time (CFU/Sample) | $< 1.0 \times 10^2$ |
| | Percent Reduction | > 99.93 % |

Figure 14

| Inoculum Concentration (CFU/0.1 mL) | *Staphylococcus aureus* ATCC 6538 |
|---|---|
| | $1.5 \times 10^5$ |

| Trial 1 | Initial Contact Time (CFU/Sample) | $1.5 \times 10^5$ |
|---|---|---|
| | 24 Hour Contact Time (CFU/Sample) | $< 1.0 \times 10^2$ |
| | Percent Reduction | > 99.93 % |

| Trial 2 | Initial Contact Time (CFU/Sample) | $1.5 \times 10^5$ |
|---|---|---|
| | 24 Hour Contact Time (CFU/Sample) | $< 1.0 \times 10^2$ |
| | Percent Reduction | > 99.93 % |

| Trial 3 | Initial Contact Time (CFU/Sample) | $1.5 \times 10^5$ |
|---|---|---|
| | 24 Hour Contact Time (CFU/Sample) | $< 1.0 \times 10^2$ |
| | Percent Reduction | > 99.93 % |

Figure 15

| Inoculum Concentration (CFU/0.1 mL) | | Staphylococcus aureus ATCC 6538 | Klebsiella pneumoniae ATCC 4352 |
|---|---|---|---|
| | | $1.5 \times 10^5$ | $1.8 \times 10^5$ |
| Trial 1 | Initial Contact Time (CFU/Sample) | $1.5 \times 10^5$ | $1.8 \times 10^5$ |
| | 24 Hour Contact Time (CFU/Sample) | $2.2 \times 10^5$ | $9.8 \times 10^4$ |
| | Percent Reduction | NR | NR |
| | | | |
| Trial 2 | Initial Contact Time (CFU/Sample) | $1.5 \times 10^5$ | $1.8 \times 10^5$ |
| | 24 Hour Contact Time (CFU/Sample) | $2.3 \times 10^5$ | $1.7 \times 10^5$ |
| | Percent Reduction | NR | 5.56 % |

Figure 17

|  | Number of Animals | | |
|---|---|---|---|
| Treatment Group | 1 Week (Histopathology, pressure test) | 6 Month (MRI, Histopathology, pressure test) | 6 Month Histopathology Only |
| Formulation 1 | 3 | 4 | 1 |
| Control | 3 | 3 | 1 |

Figure 18

|  | Animal Number | Initial ICP (cm H$_2$O) | Maximum ICP (cm H$_2$O) | CSF Leakage[a] | Peridural Adhesions[b] |
|---|---|---|---|---|---|
| Formulation 1 Group | 001 | 16 | 68 | No leaks | 0 |
|  | 002 | 16 | 54 | No leaks | 0 |
|  | 003 | 18 | 61 | No leaks | 0 |
|  |  |  |  |  |  |
| Control Group | 009 | 14 | NA | Baseline | 1 |
|  | 010 | 12 | NA | Baseline | 2 |
|  | 011 | 12 | NA | Baseline | 2 |
|  |  |  |  |  |  |

[a]Baseline indicates that CSF was leaking when the bone flap was removed.
[b]0 = Bone flap easily removed; no adhesions present. 1 = Bone flap removal not difficult. Minimal adhesions present. 2 = Moderate difficulty removing bone flap. 3 = Moderate adhesions present.
NA=Not applicable

Figure 19

|  | Animal Number | Initial ICP (cm H$_2$0) | Maximum ICP (cm H$_2$0) | CSF Leakage[a] |
|---|---|---|---|---|
| Formulation 1 Group | 004 | 11 | 63 | No leaks |
|  | 005 | 5 | 67 | No leaks |
|  | 006 | 10 | 64 | No leaks |
|  | 007 | 11 | 63 | No leaks |
|  |  |  |  |  |
|  |  |  |  |  |
| Control Group | 012 | 3 | NA[c] | NA[c] |
|  | 013 | 4 | 64 | No leaks |
|  | 014 | NA[d] | NA[d] | NA[d] |
|  |  |  |  |  |

CROSSLINKED POLYALKYLENEIMINE HYDROGELS WITH TUNABLE DEGRADATION RATES

RELATED APPLICATIONS

This application claims the benefit of priority to U.S. Provisional Patent Application Ser. No. 61/028,288, filed Feb. 13, 2008; the contents of which is hereby incorporated by reference.

BACKGROUND

Sealants, adhesives and mechanical barriers play an important role in helping patients recover from surgery or trauma. Sealants, adhesives and mechanical barriers are useful in treating patients suffering from a variety of in vivo (e.g., internal) or topical conditions, including lacerations, tears, wounds, ulcers, anastamoses, and surgical procedures. Sealants or adhesives can generally be used in any indication or application for which a suture or staple is presently used, and the sealant or adhesive often provides a better outcome than a suture or staple. Sealants or adhesives can also be applied more quickly to the injury site and often provide a better seal over the wound and healing. Various medicinal applications for sealants, adhesives and mechanical barriers are described below.

Skin Lacerations

Skin lacerations are tears in the skin produced by accidents, trauma, or as a result of a surgical procedure. Lacerations often require treatment in order to close the hole in the skin, stop bleeding, and prevent infection. Minor lacerations in the skin may be treated using an adhesive tissue to cover the wound. However, larger lacerations often require sutures or a glue to help seal the wound. For example, it is generally recommended that sutures or a glue be used to treat lacerations deeper than 0.25 inches having a jagged edge or loose flap of tissue. The location of the laceration may also affect the form of treatment. For example, it is advantageous to treat a skin laceration on a joint using a glue because an adhesive bandage tends to limit mobility of the joint. The use of sutures or glues to treat skin lacerations can also reduce the chance of scar formation.

Liver Lacerations

Lacerations of the liver can occur from trauma or as a result of a surgical procedure. The liver is a highly vascularized organ and bleeds profusely when lacerated or traumatized. Liver lacerations are difficult to repair owing to the nature of liver tissue. Liver tissue has very weak cohesive strength, and, consequently, sutures and staples are not satisfactory because they may pull through the liver tissue. The lack of satisfactory wound treatment methods for liver lacerations combined with the fact that it is difficult to reach the arteries that feed the liver renders liver lacerations particularly serious. In fact, severe lacerations of the liver often result in the patient's death due to bleeding. Thus, new materials to treat liver lacerations are needed.

Lung Surgery

The sealants and methods of the present invention are useful in lung surgery. Types of lung surgery include lobectomy, lung biopsy, lung-tissue removal, and pneumonectomy. Risks associated with lung surgery include wound infection; post-surgical internal bleeding; air leaks; pain or numbness at the incision site; and infection of the lungs (pneumonia). Further, air leakage is frequently observed after thoracic procedures, such as pulmonary resection and decortication. It is important to create an air-tight seal so as to prevent or reduce severe complications, such as bronchopleural fistulas and infection resulting from extended chest tube drainage, extended recovery time, and postoperative morbidity related to pulmonary surgery. The sealants and methods of the invention should decrease or eliminate some of the problematic aspects of lung surgery, such as treatment of pneumothorax and pulmonary leaks.

Cornea—Corneal Lacerations/Perforations

Corneal perforations are produced by a variety of medical conditions (e.g., infection, inflammation, xerosis, neurotrophication, and degeneration) and traumas (chemical, thermal, surgical, and penetrating). Unfortunately, corneal perforations often lead to loss of vision and a decrease in an individual's quality of life. Depending on the type and the origin of the perforation, different treatments may be effective, ranging from suturing the wound to a cornea graft. However, the surgical procedures are difficult given the delicate composition of the cornea and the severity of the wound which increase the likelihood for leakage and severe astigmatism after surgery. In certain cases, for example, perforations that cannot be treated by standard suture procedures, tissue adhesives (glues) are used to repair the wound. This type of treatment is very attractive because the method is simple, quick and safe, and corresponds to the requirement of a quick restoration of the integrity of the globe, avoiding further complications. Besides an easy and fast application on the wound, the characteristics of an adhesive include: 1) bind to the tissue (necrosed or not, very often wet) with an adequate adhesion force; 2) be non-toxic; 3) be biodegradable or resorbable; 4) be sterilizable; and 5) not interfere with the healing process.

Various alkyl-cyanoacrylates are available for the repair of small perforations. However, these "super glues" present major inconveniences. Their monomers, in particular those with short alkyl chains, can be toxic, in part due to their ability to produce formaldehyde in situ. They also polymerize too quickly leading to applications that might be difficult and, once polymerized, the surface of the glue is rough and hard which leads to patient discomfort and a need to wear contact lens. Even though cyanoacrylate is tolerated as a corneal sealant, a number of complications have been reported including cataract formation, corneal infiltration, glaucoma, giant papillary conjunctivitis, and symblepharon formation. Furthermore, in more than 60% of the patients, additional surgical intervention is needed.

Other glues have also been developed. Adhesive hemostats, based on fibrin, are usually constituted of fibrinogen, thrombin and factor XIII. Systems with fibrinogen and photosensitizers activated with light are also being tested. If adhesive hemostats have intrinsic properties which meet the requirements for a tissue adhesive, then autologous products (time consuming in an emergency) or severe treatments before clinical use are needed to avoid any contamination to the patient. An ideal sealant for corneal perforations should 1) not impair normal vision, 2) quickly restore the intraocular pressure (IOP), 3) maintain the structural integrity of the eye, 4) promote healing, 5) adhere to moist tissue surfaces, 6) possess solute diffusion properties which are molecular weight dependent and favorable for normal cornea function, 7) possess rheological properties that allow for controlled placement of the polymer on the wound, and 8) polymerize under mild conditions.

The use of sutures has limitations and drawbacks. First, suture placement itself inflicts trauma to corneal tissues, especially when multiple passes are needed. Secondly, although suture material has improved, sutures such as 10-0 nylon (which is the suture of choice in the cornea and elsewhere) can act as a nidus for infection and incite corneal inflammation and vascularization. With persistent inflammation and vascularization, the propensity for corneal scarring increases. Thirdly, corneal suturing often yields uneven healing and resultant regular and irregular astigmatism. Postoperatively, sutures are also prone to becoming loose and/or broken and require additional attention for prompt removal. Finally, effective suturing necessitates an acquired technical skill that can vary widely from surgeon to surgeon and can also involve prolonged operative time.

Cornea—Corneal Transplants

During a corneal transplant or penetrating keratoplasty surgery the diseased cornea is removed with a special round cutting tool called a trephine. The donor cornea is cut to a matching size. Then, the donor cornea is placed upon the eye and secured in place with approximately 16 sutures around the transplant to secure the new cornea in place. A sutureless procedure would be highly desirable because sutures are associated with the following drawbacks and others: (1) sutures provide a site for infection, (2) the sutured cornea takes 3 months to heal before the sutures need to be removed, and (3) the strain applied to the new cornea tissue from the sutures can distort the cornea. An ocular adhesive may also serve as an adjuvant to sutures and/or reduce the necessary number of sutures.

Cornea—Clear Corneal Incision

Clear corneal incisions in the temporal cornea offer several advantages with phacoemulsification. The major advantage associated with phacoemulsification is the reduction in size of the entrance wound. Smaller wounds require fewer sutures or even no sutures at all, minimizing induction of astigmatism, decreasing bleeding and subconjunctival hemorrhage, and speeding the recovery of visual acuity. See Agapitos, P. J. Curr. Opin. Opthalmol. 1993, 4, 39-43 and Lyle, W. A.; Jin, G. J. J. Cataract Refract. Surg. 1996, 22, 1456-1460. Surgeons typically examine the clear corneal incisions at the completion of the procedure by inflating the anterior chamber with balanced salt solution and applying pressure to the anterior cornea to check for leakage from the wound. If there is some leakage, the wound may be hydrated with balanced saline solution to seal fully the wound. This is done by injecting balanced saline solution into the open stromal edges. Hydration forces the two edges of the wound together, creating a tight seal. The endothelial cell pump can then remove the fluid from both the anterior and posterior portions of the wound, further sealing the wound together. See Fine, I. H. *J. Cataract Refract. Surg.* 1991, 17 (Suppl), 672-676. These tests for fluid flow, however, make several assumptions, including that the eye will remain well pressurized during the early postoperative period, that the hydrated wound will not be rapidly deturgesced by the corneal endothelium, and that the absence of aqueous outflow from the wound correlates with the inability of surface fluid from the tear film to flow into the wound, possibly contaminating the aqueous humor and predisposing to infection. However, intraocular pressure is known to vary in the postoperative period, frequently dropping to less than 5 mm Hg, and telemetric intraocular pressure monitoring devices suggest that large fluctuations in intraocular pressure occur in individual eyes in response to blinking. See Shingleton, B. J.; Wadhwani, R. A.; O'Donoghue, M. W.; Baylus, S.; Hoey, H. *J. Cataract Refract. Surg.* 2001, 27, 524-527 and Percicot, C. L.; Schnell, C. R.; Debon, C.; Hariton, C. *J. Pharmacol. Toxicol. Methods* 1996, 36, 223-228.

In a recent study, optical coherence tomography (OCT) confirmed the morphology of clear corneal incision wounds was not constant but varied in response to changes in the intraocular pressure. See McDonnell, P. J.; Taban, M.; Sarayba, M.; Rao, B.; Zhang, J.; Schiffman, R.; Chen, Z. P. *Opthalmology* 2003, 110, 2342-2348. When the eyes were well pressurized (20 mm Hg or higher), the chambers were deeply formed, and the wound edges were well apposed. Elevation of intraocular pressure up to 40 to 50 mm Hg did not result in any separation of the wound edges. As the intraocular pressure was reduced to 10 mm Hg and below, the wound edges progressively separated. The separation began at the internal aspect of the wound, with posterior migration of the posterior and peripheral wound leaflet. This separation resulted in a wedge-shaped gaping in the internal aspect of the incision. Coincident with this wound margin separation, the spontaneous flow of aqueous humor through the wound was observed, and the chamber became shallower. Elevating the intraocular pressure resulted in prompt closure of the corneal wound at its superficial margin, termination of fluid leakage from the wound, and deepening of the anterior chamber. India ink was also applied to the surface of the cornea and quickly became visible through the operating microscope within the clear corneal incisions. Histologic examination of the wounds confirmed partial penetration of India ink particles along the edges of the incisions in every cornea. These studies demonstrated that a transient reduction of intraocular pressure might result in poor wound apposition in clear corneal incisions, with the potential for fluid flow across the cornea and into the anterior chamber, with the attendant risk of endophthalmitis. See McDonnell, P. J.; Taban, M.; Sarayba, M.; Rao, B.; Zhang, J.; Schiffman, R.; Chen, Z. P. *Opthalmology* 2003, 110, 2342-2348.

Nonetheless, a progressive increase in the percentage of surgeons preferring self-sealing clear corneal incisions over scleral tunnel incisions in the United States and Europe has occurred over the past decade. See Learning, D. V. *J. Cataract Refract. Surg.* 1995, 21, 378-385 and Learning, D. V. *J. Cataract Refract. Surg.* 2001, 27, 948-955. Some studies, however, reveal an increased incidence of postoperative endophthalmitis after clear corneal cataract incisions and a recent, retrospective, case-controlled study, reported that clear corneal incisions were a statistically significant risk factor for acute post-cataract surgery endophthalmitis when compared with scleral tunnel incisions. See John, M. E.; Noblitt, R. *Endophthalmitis. Scleral tunnel vs. clear corneal incision*; Slack, Inc.: Thorofare, N.J., 2001; Colleaux, K. M.; Hamilton, W. K. *Can. J. Opthalmol.* 2000, 35, 373-378; Nagaki, Y.; Hayasaka, S.; Kadoi, C.; Matsumoto, M.; Yanagisawa, S.; Watanabe, K.; Watanabe, K.; Hayasaka, Y.; Ikeda, N.; Sato, S.; Kataoka, Y.; Togashi, M.; Abe, T. *J. Cataract. Refract. Surg.* 2003, 29, 20-26; Stonecipher, K. G.; Parmley, V. C.; Jensen, H.; Rowsey, J. J. *Arch. Opthalmol.* 1991, 109, 1562-1563; Lertsumitkul, S.; Myers, P. C.; O'Rourke, M. T.; Chandra, J. *Clin. Exp. Opthalmol.* 2001, 29, 400-405; and Blake, A. C.; Holekamp, N. M.; Bohigian, G.; Thompson, P. A. *Am. J. Opthalmol.* 2003, 136, 300-305. The visual outcome following severe endophthalmitis is always guarded. In a Western Australian Endophthalmitis Study more than half of the subjects suffered visual impairment, with 41% poorer than 20/200, 53% poorer than 20/125, and 58% poorer than 20/40. See Semmens, J. B.; Li, J.; Morlet, N.; Ng, J. *Clin. Exp. Opthalmol.* 2003, 31, 213-219. Post-cataract endophthalmitis remains a potentially blinding complication of a sight-restoring procedure.

Refractive Surgery—Laser-Assisted In Situ Keratomileusis (LASIK)

Laser-assisted in situ keratomileusis is the popular refractive surgical procedure where a thin, hinged corneal flap is created by a microkeratome blade. This flap is then moved aside to allow an excimer laser beam to ablate the corneal stromal tissue with extreme precision for the correction of myopia (near-sightedness) and astigmatism. At the conclusion of the procedure, the flap is repositioned and allowed to heal. However, with trauma, this flap can become dislocated prior to healing, resulting in flap striae (folds) and severe visual loss. When this complication occurs, treatment involves prompt replacement of the flap and flap suturing. The use of sutures has limitations and drawbacks as discussed above. These novel adhesives could also play a useful role in the treatment of LASIK flap dislocations and striae (folds). These visually debilitating flap complications are seen not uncommonly following the popular procedure LASIK, and are currently treated by flap repositioning and suturing (which require considerable operative time and technical skill). A tissue adhesive could provide a more effective means to secure the flap.

Refractive Surgery—Lens Replacement

Cataracts or other diseases or injuries that lead to poorly functioning or damaged lens require the natural lens to be replaced. The optical properties of the normal eye lens are the consequence of a high concentration of proteins called "crystallins" forming a natural hydrogel. In vertebrate lenses, a range of differently sized protein assemblies, the alpha-, beta- and gamma-crystallins, are found creating a medium of high refractive index. The anatomical basis of accommodation includes the lens substance, lens capsule, zonular fibers, ciliary muscle and the elastic part of the choroid. Accommodation occurs through accurately controlled adjustments in the shape and thickness of the lens. The capsular bag is essential in transmitting the various extralenticular forces to the lens substance.

Modern cataract surgery can be done through a small incision (usually 2.5-3.5 mm). Once the incision is made, the anterior chamber is filled with a viscoelastic and the capsular bag is pricked with a needle. From this incision, a small continuous circular capsulorhexis (CCC) approximately 1.5 mm in diameter is performed using capsulorhexis forceps. Next endocapsular phacoemulsification is performed and the lens epithelial cells are removed by aspiration.

The normal function of the lens is to focus light onto the retina. Since removing the cataract leaves the eye without a lens to focus light, an artificial (intraocular) lens is commonly placed inside the eye. Most intraocular lenses are made of plastic, silicone, or acrylic compounds; have no moving parts; and last for the remainder of a person's life. These intraocular lens implants are held in place by the posterior capsule are not able to provide ocular accommodation. Refilling the lens capsule with in situ crosslinking materials described herein offers the potential to produce a synthetic hydrogel with mechanical properties similar to the lens of a twenty year old.

As such, the invention describes materials that reproduce the properties of the natural lens and these synthetic hydrogels maintain the integrity of the capsule to gain partial or full accommodation and restore vision to the patient. Alternatively, the dendritic polymers of the invention are incorporated in current IOL materials, such as PMMA, to alter hydrophilicity, water transport, refractive index, mechanical properties or biological response.

Retina—Retinal Holes

Techniques commonly used for the treatment of retinal holes, such as cryotherapy, diathermy and photocoagulation, are unsuccessful in the case of complicated retinal detachment, mainly because of the delay in the application and the weak strength of the chorioretinal adhesion. Cyanoacrylate retinopexy has been used in special cases. It has also been demonstrated that the chorioretinal adhesion is stronger and lasts longer than the earlier techniques. As noted previously with regard to corneal perforation treatment, the extremely rapid polymerization of cyanoacrylate glues (for example, risk of adhesion of the injector to the retina), the difficulty to use them in aqueous conditions and the toxicity are inconveniences and risks associated with this method. The polymerization can be slowed down by adding iophendylate to the monomers but still the reaction occurs in two to three seconds. Risks of retinal tear at the edge of the treated hole can also be observed because of the hardness of cyanoacrylate once polymerized.

Retina—Vitrectomy/Sclerotomy Incisions

The vitreous is a normally clear, gel-like substance that fills the center of the eye. It makes up approximately ⅔ of the eye's volume, giving it form and shape before birth. Certain problems affecting the back of the eye may require a vitrectomy, or surgical removal of the vitreous. During a vitrectomy, the surgeon creates small incisions/punctures in the eye (sclerotomies) for separate instruments. These incisions are placed in the pars plana of the eye, which is located just behind the iris but in front of the retina. The instruments which pass through these incisions include a light pipe, an infusion port, and the vitrectomy cutting device. Upon completion of pars plana vitrectomy, each sclerotomy site is closed with a single interrupted suture of 8-0 silk or 7-0 polyglycolic acid suture. After a vitrectomy, the eye is filled with fluid until the vitreous is replaced as the eye secretes aqueous and nutritive fluids.

Some of the most common eye conditions that require vitrectomy include: 1) complications from diabetic retinopathy, such as retinal detachment or bleeding, 2) macular hole, 3) retinal detachment, 4) pre-retinal membrane fibrosis, 5) bleeding inside the eye (vitreous hemorrhage), 6) injury or infection, and 7) certain problems related to previous eye surgery.

Glaucoma—Filtering Bleb

Leaking filtering blebs after glaucoma surgery are difficult to manage and can lead to serious, vision-threatening complications. Filtering blebs can result in hypotony and shallowing of the anterior chamber, choroidal effusion, maculopathy, retinal, and choroidal folds, suprachoroidal hemorrhage, corneal decompensation, peripheral anterior synechiae, and cataract formation. A filtering bleb can also lead to the loss of bleb function and to the severe complications of endophthalmaitis. The incidence of bleb leaks increases with the use of antimetabolites. Bleb leaks in eyes treated with 5-fluorouracil or mitomycin C may occur in as many as 20 to 40% of patients. Bleb leaks in eyes treated with antimetabolities may be difficult to heal because of thin avascular tissue and because of abnormal fibrovascular response. If the leak persists despite the use of conservative management, a 9-0 to 10-0 nylon or absorbable suture on a tapered vascular needle can be used to close the conjunctival wound. In a thin-walled or avascular bleb, a suture may not be advisable because it could tear the tissue and cause a larger leak. Fibrin adhesives have been used to close bleb leaks. The adhesive is applied to conjunctival wound simultaneously with thrombin to form a fibrin clot at the application site. The operative field must be dry during the application because fibrin will not adhere to wet tissue. Cyanoacrylate glue may be used to close a conjuctival opening. To apply the glue, the surrounding tissue must be dried and a single drop of the cyanoacrylate is placed. The operative surgeon must be careful not to seal the applicator to the tissue or to seal surrounding tissue with glue given its quick reaction. A soft contact lens is then applied over the glue to decrease patient discomfort. However, this procedure can actually worsen the problem if the cyanoacrylate tears from the bleb and causes a larger wound.

Oculoplastics—Blepharoplasty Incisions

Blepharoplasty is an operation to remove excess skin and fat, and to reinforce surrounding muscle and tendons, around the eyes to correct droopy eyelids and bagginess under the eyes. It can be performed on the upper lids and lower lids, at the same time or separately. The operation may be done using either conventional or laser techniques. For surgery on the upper eyelids, cuts are made into the natural lines and creases in the lid, and into the laughter lines at the corner of the eye. For surgery on the lower eyelids, a cut is usually made just below the eyelashes. This means the scars run along the eye's natural folds, concealing them as much as possible. Excess fat and loose skin are removed, and the cut is closed using sutures. If only fat is being removed, sometimes the cut is made on the inside of the lower eyelid, leaving no visible scar. A tissue adhesive could provide a more effective means to secure the cuts made during surgery.

Gastrointestinal Anastomosis

The sealants and methods of the present invention should be useful in gastrointestinal anastomosis procedures. Gastrointestinal anastomosis is the technique of joining two pieces of bowel together. There are many techniques for gastro-intestinal anastomosis, including both mechanical stapled techniques and hand-sutured procedures. The technique may involve a simple end-end anastomosis of two pieces of jejunum, a more complex colo-anal anastomosis, or a biliary enteric join. One problem with techniques employing sutures or staples is that leakage may occur around the sutures or staples. See, for example, Bruce et al. Br. J. Surg. 88:1157-1168 (2001) reporting leakage rates of 5-8%. However, sealants and methods of the invention could be used to supplement the sutures or staples used in intestinal anastomoses, providing a better seal that reduces leakage. Compositions and procedures for proper sealing the consequences of a failed anastomosis are severe and frequently life-threatening. Although failures can be caused by myriad factors, including poor surgical technique (e.g., sutures that were not inserted correctly; knots that were tied too tightly rendering the ends ischaemic; or incorrect use of a staple gun), the sealants and methods of the invention should decrease or eliminate some of the causes of failed gastrointestinal anastomosis procedures.

Prostatectomy Urethral-Bladder Anastomosis

The sealants and methods of the present invention should be useful in prostatectomy urethral-bladder anastomosis procedures. Prostatectomy urethral-bladder anastomosis is the technique of joining together a patient's ureter and bladder after surgical removal of his prostate gland. Failures are caused by myriad factors, including poor surgical technique (e.g., sutures that were not inserted correctly; knots that were tied too tightly rendering the ends ischaemic). The sealants and methods of the invention should decrease or eliminate some of the causes of failed prostatectomy urethral-bladder anastomosis procedures.

Cartilage, Meniscus and Disk Repair

Cartilaginous tissues play important roles in contributing to load support and energy dissipation in the joints of the musculoskeletal system. These tissues include articular cartilage which is predominantly an avascular and alymphatic tissue with very low cell-density. As a result, articular cartilage has limited capacity for self-repair following injury or aging. Degeneration of cartilage in the meniscus, intervertebral disks, or joints can lead to severe and debilitating pain in patients. Injuries to these tissues are often retained for many years and may eventually lead to more severe secondary damage. See Moskowitz, R. W., *Osteoarthritis: diagnosis and medical/surgical management.* $2^{nd}$ ed.; W.B. Saunders Company: 1984. Today, more than one million knee, hip, and shoulder joint surgical procedures are performed annually in the United States as a consequence of trauma or a lifetime of wear and tear. See Praemer, A.; Furner, S.; Rice, D. P. Musculoskeletal Conditions in the United States, American Academy of Orthopaedic Surgeons Rosemont, Ill., 1999. Despite the large number of patients suffering from cartilage degeneration, the only widely-available treatment options for cartilage degeneration are chronic administration of anti-inflammatory agents, total joint replacement, osteotomy, or allograft transplantation, each of which leads to mixed long-term results. The compositions and methods of the present invention should be useful in the treatment of such disorders and injuries.

Tissue Plane Applications

The materials of the invention can be applied to two planes of tissue and then these two tissues can be sealed together. Over time the sealant/hydrogel degrades as new tissue grows into the area. Applications include a number of cosmetic and tissue restoration surgeries. The sealant is used when the procedures involve significant tissue plane separation that may result in formation of seroma with associated complications, such as infection, e.g., general surgery procedures, such as mastectomies and lumpectomies, and plastic surgery procedures, such as abdominoplastys, rhytidectomy or rhinoplastys, mammaplasty and other cosmetic or reconstructive surgeries or procedures, forehead lifts and buttocks lifts, as well as skin grafts, biopsy closure, cleft-palate reconstruction, hernia repair, lymph node resection, groin repair, Caesarean section, laparoscopic trocar repair, vaginal tear repair, and hand surgery.

Vascular and Cardiovascular Repair

The compositions and methods of the invention may be used for repairing, closing, and/or securing vascular and cardiovascular tissue. Representative procedures include coronary artery bypass grafts, coronary angioplasty, diagnostic cardiac catheterization, carotid endarterectomy, and valve repair. An additional use of the sealant is for the repair of cardiac tissue after a myocardial infarction. The polymer would be applied to the infracted tissue to provide structural support to the weakened tissue. For example, the material would act as a sleeve for the cardiac tissue.

Repair of Dura Tissue

Dura tissue is a fibrous membrane covering the brain and the spinal cord and lining the inner surface of the skull. Standard methods of dural repair involve the application of interrupted sutures and the use of dural replacement materials (duraplasty). This is a meticulous surgery and suffers from the limitation that pinholes produced by surgical needles can cause leakage. Moreover, intraoperative dehydration can shrink the dura creating a difficult closure since it is difficult to approximate the edges with sutures. In older patients, the dura is often more susceptible to tearing when stretched and/or sutured because the dura can be thin and fragile. Adhesives such as fibrin have been explored for repair of dura tissue, but have had limited success. See "Glue in the Repair of Dural Defects in Craniofacial Resections," *J. Latyngology and Otology* 1992, 106, 356-57; Kjaergard et al., "Autologous Fibrin Glue Preparation and Clinical Use in Thoracic Surgery," *Eur. J. Cardio-Thorc. Surg.* 1992, 6, 52-54; Thompson et al., "Fibrin Glue: A Review of Its Preparation, Efficacy, and Adverse Effects as a Topical Hemostat," *Drug Intelligence and Clinical Pharmacy* 1988, 22, 946-52; and Brennan, "Fibrin Glue," *Blood Reviews* 1991, 5, 240-44. The sealants and methods of the present invention should be useful in repairing the dura after a craniotomy or laminectomy and prevent postoperative leakage of cerebrospinal fluid. See Preul et al. *Neurosurgery* 2003, 53, 1189-1199 and Balance, C. A. in "Some Points in the Surgery of the Brain and Its Membranes" London, Macmillan & Co.

Injection Site Wound

Many therapeutic agents are administered to a patient by injection. However, one complication of this procedure is that the tissue at the injection site can become infected or susceptible to poor healing. One clinical situation where infections are prone to occur is when a therapeutic agent is injected into the eye of a patient. This mode of administration is used in the treatment of age-related macular degeneration (AMD) and results in about 2% of patients suffering from infection or endophthalmitis.

Age-related macular degeneration is a disease that blurs the sharp, central vision needed for "straight-ahead" activities such as reading and driving. Specifically, AMD is a progressive disease of the retina where the light-sensing cells in the central area of vision (the macula) stop working and eventually die. The disease is caused by a combination of genetic and environmental factors, and it is most common in people who are age sixty and over. In fact, AMD is the leading cause of visual impairment in the elderly population. It is estimated that fifteen million people in the United States have AMD, with approximately two million new cases diagnosed annually. There are two types of AMD—wet and dry. Wet AMD occurs when abnormal blood vessels behind the retina start to grow under the macula. These new blood vessels tend to be very fragile and often leak blood and fluid. The blood and fluid raise the macula from its normal place at the back of the eye. Damage to the macula occurs rapidly and loss of central vision can occur quickly. On the other hand, dry AMD occurs when the light-sensitive cells in the macula slowly break down, gradually blurring central vision in the affected eye. Central vision is gradually lost. In this disease, Vascular Endothelial Growth Factor (VEGF) is a key growth factor, which promotes the new growth blood vessels. Currently, it is believed that that when the retinal pigment epithelial (RPE) cells begin to wither from lack of nutrition (i.e., ischemia), VEGF is up-regulated and new vessels are created. Yet, the vessels do not form properly and leaking results. This leakage causes scarring in the macula and eventual loss of central vision. To prevent or inhibit this neovascularization process, antiangiogenic drugs are given the patient. In most cases, the drugs are injected into the vitreous of the eyeball, then pass into the subretinal space where the vessels proliferate. These drugs include mucagenm squalamine lactate, combretastatin 4 prodrug, and avastin.

The sealants and methods of the present invention should be useful in sealing injection site wounds. Among the various possibilities, the injection can be given and then the sealant applied to the injection site, or alternatively the sealant can be applied and then the injection can be done through the sealant.

Therapeutic Use of Crosslinked Polyalkyleneimines

To date polyalkyleneimines (PAIs) have been used primarily as gene transfection agents with limited success. In general, large PAIs (25,000 molecular weight and higher) are more efficient at forming complexes and condensing with polynucleic acids, but their associated toxicity has also been reported to increase with increasing molecular weight. As a strategy to reduce this toxicity, polyalkylene glycols (PAGs), such as monomethoxy-polyethylene glycols, have been grafted to the PAIs in vitro before condensation with polynucleic acids. In a few cases, PAIs have been combined with difunctionally activated PEG in dilute solution to produce linear block copolymers of PAI and PAG, or in an emulsion polymerization process to produce small PAI/PAG microspheres. In both of these cases, the PAI/PAG block copolymers were synthesized in vitro for the purpose of condensing with polynucleic acids for gene transfection.

In addition, U.S. Provisional Patent Application Ser. No. 60/758,105, filed Jan. 11, 2006, U.S. Provisional Patent Application Ser. No. 60/837,199, filed Aug. 11, 2006, and U.S. patent application Ser. No. 11/653, 433, filed Jan. 11, 2007, all of which are hereby incorporated by reference in their entirety, described inter alia compositions and methods of use of crosslinked gels comprising polyalkyleneimines.

SUMMARY

One aspect of the present invention relates to methods of sealing a wound or tissue plane or filling a void space, or securing meshes, films or other devices within the body. In certain embodiments, the wound is an ophthalmic, pleural or dural wound, or a hernia repair mesh.

In certain embodiments, the compositions used to seal the wound or tissue plane comprises a crosslinking agent. In certain embodiments, the crosslinking agent is a polyalkyleneimine. In certain embodiments, the polyalkyleneimine is polyethyleneimine. In certain embodiments, treatment of the polyethyleneimine with a crosslinker causes the polyethyleneimine to polymerize to form a hydrogel seal or barrier.

In certain embodiments, the crosslinker is a polyethylene glycol having reactive terminal groups. In certain embodiments, the reactive terminal groups are activated esters, such as N-hydroxysuccinimide ester. In certain embodiments, the reactive terminal groups are isocyanates. In certain embodiments, the polyethyleneimine has a lysine, cysteine, isocysteine or other nucleophilic group attached to the periphery of the polymer.

In certain embodiments, the polyethyleneimine is mixed with a second polymer, such as a polyethylene glycol containing electrophilic groups. In certain embodiments, the compositions used to seal the wound or tissue plane are formed by reacting a polyalkyleneimine bearing nucleophilic groups with a crosslinker containing electrophilic groups. In certain embodiments, the electrophilic groups on the crosslinker are activated esters, such as N-hydroxysuccinimide esters.

Remarkably, disclosed herein is the discovery that the use of certain crosslinkers in combination with polyalkyleneimines at specific concentrations can result in hydrogels with tunable degradation properties.

BRIEF DESCRIPTION OF THE FIGURES

FIG. 3 depicts graphs showing the percent swelling of PEI or trilysine crosslinked with $PEG\text{-}(SS)_2$; and PEI or trilysine crosslinked with $PEG\text{-}(SG)_2$ (in PBS, pH 7.4, 37° C.) as a function of time.

FIG. 4 depicts graphs showing the percent swelling of PEI or trilysine crosslinked with $PEG\text{-}(SA)_2$; and PEI or trilysine crosslinked with $PEG\text{-}(SSeb)_2$ (in PBS, pH 7.4, 37° C.) as a function of time.

FIG. 5 depicts [A] a bar graph showing degradation times for various compositions (in PBS, pH 7.4, 37° C.); and [B] a bar graph showing the difference in time for a hydrogel composition to degrade visibly when using trilysine instead of PEI.

FIG. 7 depicts [A] a graph showing time to visual degradation for different PEG:PEI ratios; [B] a bar graph showing the equilibrium swelling of various compositions (in PBS, pH 7.4, 37° C.) at approximately 24 hours; and [C] a table comparing the number and type of free amines in specific crosslinking agents to the percentage observed swelling at approximately 40 hours.

FIG. 8 depicts tables showing various amounts of PEGs, linkages, and various reagents for the synthesis of difunctional N-hydroxysuccinimide activated PEGs from difunctional PEG-OH via [A] anhydrides (see Example 1) or [B] diacids (see Example 2).

FIG. 9 depicts a table summarizing various polyalkyleneimine (PAI) and polyalkyleneglycol (PAG) hydrogel formulation compositions.

FIG. 10 depicts a table outlining the data from preliminary antimicrobial investigations of formulation 1 and formulation 3.

FIG. 11 depicts a table outlining different properties of formulation 1, formulation 2, and formulation 3.

FIG. 12 depicts a table showing the data from antimicrobial investigations of formulation 1. The experiment was repeated in triplicate.

FIG. 13 depicts a table showing the data from antimicrobial investigations of formulation 2. The experiment was repeated in triplicate.

FIG. 14 depicts a table showing the data from antimicrobial investigations of formulation 3. The experiment was repeated in triplicate.

FIG. 15 depicts a table showing the data from antimicrobial investigations of formulation 4. The experiment was done twice.

FIG. 17 depicts a table showing the animal assignment and treatment schedule in the study of formulation 1 as a dural sealant.

FIG. 18 depicts a table summarizing the pressure testing prior to necroscopy on day 8 in the investigation of formulation 1 as a dural sealant.

FIG. 19 depicts a table summarizing the pressure testing prior to 6-month necroscopy (days 171/172) in the investigation of formulation 1 as a dural sealant.

DETAILED DESCRIPTION

Figure 1:
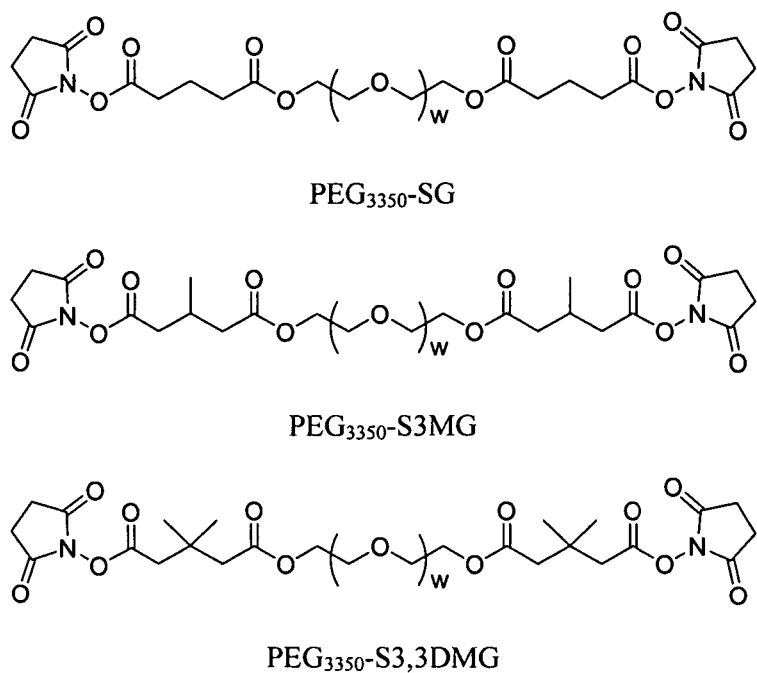
FIG. 1 depicts the structures of $PEG_{3350}\text{-}(SG)_2$, $PEG_{3350}$-S3MG and $PEG_{3350}$-S3,3DMG, as well as a table showing the properties of hydrogels formed by the combination of $PEG_{3350}\text{-}(SG)_2$, $PEG_{3350}$-S3MG and $PEG_{3350}$-S3,3DMG with $PEI_{2000}$.

Certain aspects of the invention relate to compositions and/or methods of use of crosslinked hydrogels comprising polyalkyleneimines, an example of a crosslinking agent. In particular, it is disclosed herein that the use of certain crosslinkers in combination with polyalkyleneimines at specific concentrations can result in hydrogels with tunable degradation properties.

Polyalkyleneimine Hydrogels

One aspect of the present invention relates to compositions which comprise polyalkyleneimines. These gels are prepared by reacting a polyalkyleneimine (PAI) with a crosslinker, such as an activated polyethylene glycol. The gels of the invention are amendable to a variety of clinical treatments, such as incisions created during general surgery or wounds/incisions in the dura during neurosurgery. The polyalkyleneimine gels of the invention offer the advantage that the secondary and tertiary amino groups of the gel can be converted to secondary and tertiary ammonium cations which may encourage cell attachment and cell ingrowth. In certain embodiments, the secondary and tertiary amines of the polyethyleneimine (PEI) can be converted to ammonium cations by placing the PEI in an aqueous solution.

The polyalkyleneimine (PAI) gels of the invention have superior adhesion properties. Their superior tissue-adhesion properties may be due to two factors. First, the cationic properties of PEI promote interaction with, and possibly penetration within, an anionic tissue substrate. See Rep. Prog. Phys. 1998, 61, 1325-1365. Cationic interactions could occur through the secondary and tertiary ammonium cations of the PEI backbone or through primary amino groups that did not react with the crosslinker. Second, PEI contains a large number of functional groups per molecule, thus providing an increased number of crosslinkable sites within the polymer network. The increased number of crosslinkable sites within the polymer network affords dense, interpenetrating networks between the hydrogel and the tissue surface. The number of free amino groups in the resulting hydrogel can be controlled by varying the ratio of PEI to activated PEG. The ability to control the number of free amino groups is significant because greater cell ingrowth was observed in tissue ingrowth experiments using hydrogels that contained a larger percentage of PEI. Indeed, the relative rates of ingrowth in vivo of some embodiments of the invention are discussed in Example 7.

In addition to increased adhesion, it has been found that as the molecular weight of the PEI increases from about 1,300 to about 2,000 g/mol the swelling of the resulting hydrogel decreases in certain instances. Thus, the molecular weight of the PEI may be adjusted in order to tune the swelling-effects of the resultant hydrogel.

A large variety of PAI derivatives are amenable to the present invention. For example, the amino groups of the PAI may be functionalized with a fatty acid, lower alkyl, an alkenyl, or alkynyl group. In addition, the amino groups or a portion of the amino groups may be functionalized to contain active agents, pharmaceutical agents, preservatives, radio isotopic ions, magnetically detectable ions, antibodies, medical contrast agents, colorants, dyes, or other visualization agents. In certain embodiments, about 1% to about 70% of the primary amines of the PEI are functionalized. The PAI derivatives may contain hydrolytically and/or enzymatically degradable linkages capable of releasing the functional derivatives, active agents, pharmaceutical agents, preservatives, radio isotopic ions, magnetically detectable ions, antibodies, colorants, dyes, or other visualization agents. Alternatively, a different nucleophile can be added to the PEI, such as a cysteine, isocysteine, thiol, or other such nucleophilic group. For example, a PEI can be modified such that all the primary amines are modified with a cysteine thus affording a PEI derivative which can form crosslinked gel/networks using the amine, thiol, or both the amine and thio. In certain embodiments, an ureido, urea, acetoacetoxy, RGD peptide, EDTA, or carbohydrate group may be bonded to one or more of the amino groups of the PEI. Representative carbohydrates include erythrose, threose, ribose, arabinose, xylose, lyxose, allose, altrose, glucose, mannose, gulose, idose, galactose, talose, sucrose, lactose, and the like. It is possible that the ureido group and urea group will impart adhesion partially via a cation/anion interaction. The acetoacetoxy group may adhere to tissue by making a metal complex on the surface of the tissue.

In certain embodiments, the PEI is functionalized to include thiol moieties, so that both primary amino groups (—$NH_2$) and thiol groups (—SH) could react with electrophilic groups of a crosslinker or a combination of them, such as an acrylate, succinimidyl ester, maleimide, ester, or aldehyde. The electrophilic groups can be attached to poly(alkyleneoxide) polymers (e.g., PEG, PPG or PEG-PPG). Two or more electrophilic groups are required in the crosslinker. Of course, the degree of PEI functionalization may be varied in order to obtain the desired physical properties of the resultant gel. In certain embodiments, only about 1% of the primary amino groups of the PEI are functionalized. In other instances, about 5% to about 25% of the primary amino groups of the PEI are functionalized. In other instances, about 25% to about 50% of the primary amino groups of the PEI are functionalized. In other instances, about 99% of the primary amino groups of the PEI are functionalized. In certain embodiments, one or more of the amino groups are reacted with an epoxide or acylating agent. In certain embodiments, one or more of the amino groups are reacted with an isocyanate.

The molecular weight of the PEI may be adjusted to tune the physical properties of the gel formed by addition of the crosslinker. In certain embodiments, the PEI has a weight average molecular weight of about 400 g/mol to about 2,000,000 g/mol. In certain embodiments, the PEI has a weight average molecular weight of about 400 g/mol to about 1,000,000 g/mol. In certain embodiments, the PEI has a weight average molecular weight of about 400 g/mol to about 500,000 g/mol. In certain embodiments, the PEI has a weight average molecular weight of about 400 g/mol to about 100,000 g/mol. In certain embodiments, the PEI has a weight average molecular weight of about 400 g/mol to about 50,000 g/mol. In certain embodiments, the PEI has a weight average molecular weight of about 400 g/mol to about 10,000 g/mol. In certain embodiments, the PEI has a weight average molecular weight of about 400 g/mol to about 5,000 g/mol. In certain embodiments, the PEI has a weight average molecular weight of about 400 g/mol to about 2,000 g/mol.

In certain embodiments, the polyalkyleneimine has a weight average molecular weight of about 600 to about 10,000 Daltons, the polyalkylene glycol has a weight average molecular weight of about 500 to about 20,000 Daltons, and the molar ratio of the polyalkyleneimine to the polyalkylene glycol is within a molar range of about 0.025:1 to about 3.0:1. In certain embodiments, the hydrogel reaches equilibrium swelling in about 5 to about 30 hours. In certain embodiments, the hydrogel reaches equilibrium swelling in about 18 hours.

In certain embodiments, the aforementioned polyalkyleneimine/polyalkylene glycol hydrogels may be used or modified to non-covalently carry or contain active agents, pharmaceutical agents, preservatives, radio isotopic ions, magnetically detectable ions, antibodies, medical contrast agents, colorants, dyes, or other visualization agents (see below).

Figure 2:
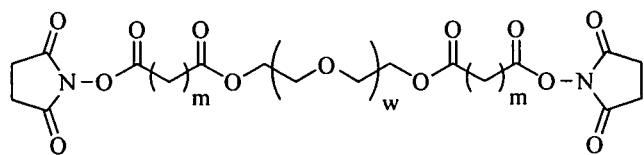
FIG. 2 depicts tables showing [A] polyethlyene glycol derivatives and crosslinking agents; and [B] the number of free amines in selected crosslinking agents.

Because charged species encourage tissue growth, the use of polyalkyleneimine-containing materials is advantageous because they allow for incorporation of a large number of charged species. The charged species are created by converting unreacted primary amines, and internal secondary and tertiary amines into ammonium cations under physiological conditions. FIG. 2B illustrates the number of primary, secondary and tertiary amines contained in various crosslinking agents based on a polymer system having eighteen primary amines. As illustrated in FIG. 2B, the trilysine crosslinking agent contains only primary amines and a pendant carboxylate while a PPI(DAB)-G1 dendrimer adds 9 units of potential cationic charge with the addition of 9 tertiary amines. The $PEI_{800}$ adds 14 units of potentially charged species (i.e., 155% more charge) compared to the PPI(DAB)-G1 dendrimer, while the $PEI_{2000}$ adds 26% more potentially charged species than $PEI_{800}$. Finally, $PEI_{25000}$ adds 24% more potentially charged species than $PEI_{2000}$, owing to the increased number of secondary and tertiary amines. Since the number of secondary and tertiary amino groups increases with increasing molecular weight of the polyalkyleneimine, the polyalkyleneimine hydrogels of the invention can be tuned by incorporating crosslinking agents of various molecular weights, and hence charge density, in order to affect the tissue ingrowth and degradation properties of the resulting hydrogel. These properties were investigated in various embodiments of the invention, and the results are discussed in Example 7.

Polyalkyleneimine hydrogels offer an advantage over other hydrogels because they should have antimicrobial and antiviral activity. Recent reports indicate that both polyalkyleneimines and derivatives thereof have antimicrobial properties, while lacking activity against mammalian cells. See *Biotechnol. Bioeng.* 2005, 90, 715-722; *Biotechnol. Bioeng.* 2003, 83, 168-172; *Biotechnology Letters* 2003, 25, 1661-1665; *Biotechnol. Prog.* 2002, 18, 1082-1086; *Chem. Commun.* 1999, 1585-1586; and *Proc. Nat. Acad. Sci. USA* 2006, 103, 17667-17671. Additionally, the antimicrobial properties of PEI are enhanced with alkylation.

Thus, hydrogels prepared from polyalkyleneimines may help fight, inhibit, prevent or even eliminate the chance for infection when applied to the tissue of a patient. Since the presence of cationic groups, especially quaternary amines, may influence the antimicrobial properties of the hydrogel, the PAI, in certain embodiments, may be derivatized with one or more quaternary amines. In certain embodiments, the PAI may be derivatized with four or more quaternary amines. In certain embodiments, the PAI may be derivatized with ten or more quaternary amines. Since the presence of cationic groups and hydrophobic side chains, when combined, tend to confer better antimicrobial properties, the PAI, in certain embodiments, may be derivatized with one or more quaternary amines and one or more fatty acid, lower alkyl, alkenyl, or alkynyl groups.

Examples 4 and 5 describe in detail the antimicrobial properties of various embodiments of the invention. Not intending to be bound by any particular theory, a certain diacid length on the PAG end-group modification may be necessary to confer significant antimicrobial properties to the hydrogel formulation. For example, two embodiments of the invention (formulations 2 and 4) were composed of the same materials at the same ratio and concentration, except that one embodiment had a glutaric acid-based structure ($C_5$) on the terminus of the PEG and another embodiment had a sebacic acid-based structure ($C_{10}$) on the terminus of the PEG. It is possible that the change to sebacic acid and the hydrophobicity associated with the longer alkyl chain may be important in conferring significant antimicrobial properties.

Furthermore, not intending to be bound by any particular theory, antimicrobial properties may also be either PAI-concentration dependent and/or dependent upon the number of free primary amines following crosslinking. Increasing the overall amount of PEI within the systems described in Examples 4 and 5 changes the hydrogel properties by moving from an excess of PEG active esters to an excess of PEI primary amines. Theoretically, if crosslinking goes to completion, formulation 1 would not have any free primary amines and the overall amount of PEI would be the lowest amongst formulations 1, 2, or 3. Both formulation 2 and formulation 3 demonstrated significant antimicrobial properties independent of PEI concentration, at least with a $10^5$ population of inoculum. These observations suggest that it is also important to have an excess of free primary amines within the cured hydrogel to confer significant antimicrobial properties. In summary, at certain ratios of PEG active esters/PEI primary amines in combination with longer alkyl chain diacids, compositions of the present invention possess remarkable antimicrobial properties.

Polyalkyleneimine hydrogels offer the additional advantage that the amino groups of the polyalkyleneimine can act as a buffering agent. The ability to control the pH during preparation of the hydrogel is important because certain pHs are optimal for crosslinking of the components. In particular, the pH of a mixture of crosslinking components can affect the rate at which the crosslinking reaction takes places. In some instances, the desired pH can be achieved by adding a buffering agent, such as phosphates, carbonates, borates, and the like, to the solution containing the crosslinking components. However, when using polyalkyleneimines as a crosslinkable component, the primary, secondary, and tertiary amines act as buffering agents to provide some buffering capacity throughout a wide range of pHs. See Junghun, S. et al. *Bioorganic Chemistry* 1994, 22, 318-327. Moreover, as the crosslinkable component reacts, some of the amines are removed from solution, thereby reducing the pH. Since quick set-times can require higher pHs, it is advantageous to use a component which influences the pH so that the pH will lower to more physiological levels soon after mixing. This buffering feature of polyalkyleneimines eliminates the need for a strong buffer to achieve the high pH-levels sometimes used in preparing a hydrogel. Notably, addition of strong buffers may not be desirable because such buffers may remain in the sealant and cause the patient's tissue to become irritated.

Crosslinkers

In certain embodiments, the materials of the invention may be formed by reacting a polyalkyleneimine (an example of a "crosslinking agent"), or other amine-containing polymer, with a crosslinker. A large number of crosslinkers are amenable to the invention. In certain embodiments, the crosslinker is an activated polyethylene glycol. In certain embodiments, the activating group is an electrophilic group. For example, in certain embodiments, the polyethylene glycol contains a N-hydroxysuccinimide ester group at each end of the polymer. In certain embodiments, the N-hydroxysuccinimide is functionalized with a sulfonic acid moiety. In certain embodiments, the polyethylene glycol contains an aldehyde at each end of the polyethylene glycol. In certain embodiments, the polyethylene glycol is a star, dendritic, or branched polymer with three or more terminal activating groups.

In certain embodiments, the polyethylene glycol crosslinker contains two or more different electrophiles. The different electrophiles may have similar or dissimilar reactivities. The different electrophiles provide linkages having similar or dissimilar degradation rates. The selection of electrophiles allows for control over the crosslinking reactions to form the hydrogels; and the adhesive properties and the degradation rate of the resulting hydrogel. For example, a polyethylene glycol can be derivatized such that one end of the polyethylene glycol contains a SPA and another end contains a SG. In this example, both electrophilic moieties are activated esters, but the degradation rates of the two resulting linkages are different under a particular set of conditions. For example, a hydrogel prepared with only PEG-(SPA)$_2$ termini is generally stable at 37° C. for more than about four months, whereas a hydrogel prepared with PEG-(SG)$_2$ termini is often stable for less than about one week. Remarkably, the stability of the hydrogel can be tuned by judicious selection of crosslinker and crosslinking agent.

In certain embodiments, more than one polyethylene glycol crosslinker can be used. For example, a hydrogel may be formed from a mixture of a crosslinking agent (e.g., PEI), and PEG-(SPA)$_2$ and PEG-(SG)$_2$. The use of different crosslinkers typically provides linkages having distinct degradation rates, thus allowing the properties of the resulting hydrogel to be controlled and manipulated. Further, the swelling profile of a gel likewise may be tuned such that the gel will swell quickly over a short period of time to a desired initial size as one crosslinker degrades from the network, followed by a longer period during which the swelling will plateau or increase gradually as the second crosslinker begins slowly to degrade.

In certain embodiments, the polyethylene glycol crosslinker is represented by the formula below, wherein w is an integer in the range from about 5 to 1,000; and m is an integer in the range from about 1 to about 50.

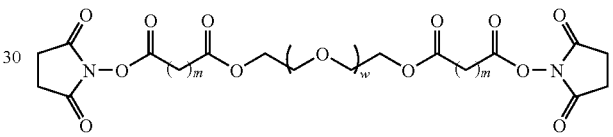

A further embodiment of the invention is the use of a chemical peptide ligation reaction to create a crosslinked gel comprising a dendritic polymer. For example, in certain embodiments, an aldehyde, aldehyde-acid or aldehyde-ester reacts with a cysteine-functionalized polymer to form a gel or crosslinked network. In certain embodiments, the dendritic polymers have nucleophilic groups, such as primary amino groups or thiol groups, which can react with electrophilic groups, such as acrylate, succinimidyl ester, maleimide, ester aldehyde, or aldehyde. In certain embodiments, the dendritic polymer has nucleophilic groups capable of reacting with an activated diester of sebacic acid.

Tuning Properties of Resulting Hydrogels by the Specific Combination of Crosslinker and Polyalkyleneimine Certain aspects of the invention relate to unexpected properties of hydrogels comprised of certain crosslinkers in combination with polyalkyleneimines, at specific concentrations.

Initial experiments provided evidence that 15 wt % PEG$_{3350}$ succinimidyl glutarate [PEG$_{3350}$-(SG)$_2$] derivatives crosslinked to polyethyleneimine, M$_w$=2000 (PEI$_{2000}$), in a ratio of 15:1 PEG:PEI (w/w), completely degraded in approximately four days in PBS at a pH of 7.4 and a temperature of 37° C. (see FIG. 1). However, for many sealant applications within the body, complete dissolution of the hydrogel in four days was not suitable since healing usually occurs on the order of weeks.

To extend this rate of hydrolysis, more sterically hindered PEG succinimidyl glutarate derivatives were synthesized and subsequently crosslinked to PEI$_{2000}$, in a ratio of 15:1 (w/w), to make 15 wt % hydrogels. Counterintuitively, the derivatized gels degraded more quickly than the underivatized succinimidyl glutarate. The rapid degradation of hydrogels containing the crosslinker PEG succinimidyl glutarate and its derivatives, when combined with a polyalkyleneimine (PAI) crosslinking agent, was unexpected since other hydrogel systems containing a PEG succinimidyl succinate (PEG-$(SS)_2$) or PEG succinimidyl glutarate (PEG-$(SG)_2$) have been reported to swell and then retain certain properties for at least three days before degrading on the order of a few weeks. For example, Confluent Surgical's DuraSeal, a dural sealant composed of $PEG_{10000}$-$(SG)_4$ and trilysine, was prepared according to IFU and the samples were monitored gravimetrically while swelling in PBS at a pH of 7.4 and a temperature of 37° C. The crosslinked gels of $PEG_{10000}$-$(SG)_4$ and trilysine swelled approximately 115% and then slowly degraded (determined by gravimetrically by incremental uptake in water) over 21 days, the gels remained visible for 29 days, but they could not be isolated and weighed.

To determine the unexpected cause of accelerated degradation with the polyalkyleneimine crosslinking agent, various crosslinkers and crosslinking agents were procured to determine which variable was leading to accelerated degradation.

For instance Lys-Lys-Lys (trilysine) was procured and combined with $PEG_{3350}$-$(SG)_2$, in a ratio of 14.6:1 PEG:Trilysine (w/w), to make a 15 wt % hydrogel that set in 22 seconds. These samples swelled to approximately 121% at equilibrium (approximately 24 hours) and then slowly degraded over 10 to 13 days in a manner similar to the $PEG_{10000}$-$(SG)_4$ and trilysine system described above.

Next, $PEI_{2000}$ was combined with $PEG_{10000}$-$(SG)_4$ in a ratio of 46.1:1 PEG:Trilysine (w/w), to make a 15 wt % hydrogel that set in 18 seconds. Theses samples swelled to approximately 150% at equilibrium (approximately 24 hours) and then rapidly degraded in three to four days in a manner similar to the $PEG_{3350}$-$(SG)_2$ and $PEI_{2000}$ system discussed above.

Finally, a first generation polypropyleneimine dendrimer with a diaminobutane core [G1-PPI(DAB)], a small polyalkyleneimine crosslinking agent having a similar molecular weight and number of primary amines such as Lys-Lys-Lys, were combined with $PEG_{3350}$-$(SG)_2$ at a ratio of 29.3:1 PEG:PPI (w/w), to make a 15 wt % hydrogel that set in approximately 7 seconds. These samples swelled to approximately 158% at equilibrium (approximately 24 hours) and then rapidly degraded in two to three days in a manner similar to the $PEG_{3350}$-$(SG)_2$ and $PEI_{2000}$ system described above.

Surprisingly, throughout these experiments, and other experiments using various molecular weight PEI polymers not disclosed herein, the inclusion of a polyalkyleneimine crosslinking agent appeared to lead to more rapid degradation independent of the molecular weight of the crosslinking agent. It was therefore hypothesized that the enhanced rate of degradation might be due to the local environment created by the presence of secondary and tertiary amines and any unreacted primary amines (and/or their respective ammonium cations on the polyalkyleneimine crosslinking agents). Although not intending to be bound by a particular theory, it is possible that the amines on the polyalkyleneimine crosslinking agents might either raise the pH of the local environments surrounding the ester linkages or complex with the ester derivative, thereby catalyzing ester hydrolysis. Furthermore, the polyalkyleneimines may take part in acyl transfer reactions.

With the aim of extending the degradation time for gels containing ester linkages, taking into account the observation that more sterically hindered glutarate derivatives did not lengthen degradation rates, it was hypothesized that increasing the carbon spacer length between the terminal diacid derivatives on PEG, already known to stabilize activated ester derivatives (see U.S. Pat. No. 5,672,662; hereby incorporated by reference in its entirety), would slow the rate of degradation of hydrogels containing polyalkyleneimine crosslinking agents. Similar observations relating to extending degradation times by increasing alkyl moiety length within diacid chains have been reported in the literature (see, Venkata N. M., et al. *Trends Biomater. Artif. Organs* 2004, 18, 52-59). These observations have generally been attributed to changes in hydrolytic degradation based on hydrophobicity. Although again not intending to be bound by a particular theory, it is possible that not only are the degradation times increased with increasing hydrophobicity, due to increased alkyl moiety length of the diacid chains, but the degradation times may also be increased due to increased spacing between the ester functionality and the environment created by the presence of the polyalkyleneimine crosslinking agents.

To test this hypothesis, a series of activated polyalkylene glycol diacid derivatives were synthesized and the activated crosslinkers were combined with a polyalkyleneimine or Lys-Lys-Lys crosslinking agents to further demonstrate and appreciate the criticality of certain crosslinkers in combination with polyalkyleneimines and the manner in which polyalkyleneimines influence the hydrolytic degradation process (see FIG. 4). Since all of the previously tested polyalkyleneimine crosslinking agents had led to more rapid degradation, independent of the molecular weight of the crosslinking agent and the presence and/or ratio of primary, secondary, and tertiary amines (or their respective ammonium cations), polyethyleneimine with a molecular weight of 2000 ($PEI_{2000}$) was used in the following experiments as the representative polyalkyleneimine. However, it is understood that any of the observations with reference to formulations containing $PEI_{2000}$ should also be applicable to other formulations containing polyalkyleneimines as previously mentioned.

The crosslinking agent solution for the two cross-linking agents of interest were held constant for each activated polyethylene glycol derivative. The solution was prepared to produce a 15 wt % gel with ratio of activated esters on the crosslinker to primary amines on the crosslinking agent of either 0.75:1 for the $PEI_{2000}$ crosslinking agent or 1:1 for the Lys-Lys-Lys crosslinking agent. These ratios produced the lowest swelling gels for each crosslinking agent. The resulting hydrogels from each specified combination were placed in phosphate buffered saline (PBS) at a pH of 7.4 and a temperature of 37° C. The gels were removed from solution, blotted dry, and weighed periodically to determine a gravimetric change in mass and the bathing solution from each hydrogel was changed after each weighing. The percent swelling of each hydrogel was determined using the following equation (1):

$$\% \text{ Swelled}=[(M_x-M_o)/M_o]*100 \quad (1)$$

where $M_o$ represents the initial mass of the hydrogel and $M_x$ represents the observed mass of the hydrogel exposed to the bathing solution after a known length of time. The percent swelling over time was recorded in triplicate for each combination. The gradual increase in percent swelling over time was attributed to degradation within the polymer network.

Many of the hydrogels in this study underwent a rapid change in percent swelling over approximately the first 16 to 24 hours (referred to as equilibrium swelling which is a common phenomenon across most hydrogel compositions) and then degraded over various periods of time (See FIGS. 3 and 4). However, the gels composed of the crosslinker $PEG_{3350}$-(succinimidyl succinate)$_2$ [$PEG_{3350}$-$(SS)_2$] experienced a much quicker degradation in which the $PEI_{2000}$ crosslinking agent compositions degraded at a more rapid rate than water uptake, completely degrading in less than 6 hours. The gels composed of $PEG_{3350}$-$(SS)_2$ and the Lys-Lys-Lys crosslinking agent also degraded rapidly, but the gels remained cohesive and measurable for up to 24 hours and visibly degraded within 45 hours.

Interestingly, the hydrogels exhibited a decrease in the rate of degradation and a trend toward decreased swelling as the carbon spacer length of the diacid was increased. While this observation was predicted based on previous reports, it was unexpected that the hydrogel formulations with a common crosslinker composition degraded more rapidly with a crosslinking agent composition of $PEI_{2000}$ versus the crosslinking agent composition of Lys-Lys-Lys. Moreover, as the carbon spacer length of the diacid was increased, the relative difference in the rate of degradation decreased. In other words, with an increase in the carbon spacer length of the diacid, the difference in the composition of the crosslinking agent became less important. These observations supports the hypothesis that the degradation times may be enhanced due to increased spacing between the ester functionality and the environment created by the presence of the polyalkyleneimine crosslinking agents.

This point is further confirmed by examining the time it took various hydrogel compositions to completely degrade using various crosslinkers and the crosslinking agents $PEI_{2000}$ or Lys-Lys-Lys (see FIG. 5A). As the carbon spacer length of the diacid increases, both formulations experienced a decrease in the rate of degradation, but the difference between the rates of degradation among any crosslinker composition was also highly affected by the crosslinking agent. For instance, a hydrogel composed of $PEG_{3350}$-$(SS)_2$ degrades 650% more slowly when the crosslinking agent is switched from $PEI_{2000}$ to Lys-Lys-Lys. As the length of the diacid increases, this difference becomes almost insignificant with a hydrogel composed of $PEG_{3350}$-(succinimidyl sebecate)$_2$ [$PEG_{3350}$-$(SSeb)_2$] degrading 16% more slowly when the crosslinking agent is switched from $PEI_{2000}$ to Lys-Lys-Lys (See FIG. 5B).

Not only is the carbon spacer length of the diacid important, the concentration of the crosslinking agent is also critical, remarkably. From the previous experiments, the degradation times were thought to be enhanced due to increased spacing between the ester functionality and the environment created by the presence of the polyalkyleneimine crosslinking agents. In other words, the polyalkyleneimine crosslinking agents appear to catalyze the degradation of the hydrogel. This observation/hypothesis is similar to other experiments with poly amines and polyethyleneimines (e.g., Everaerts, A. et al. *Die Makromolekulare Chemie* 1984, 185, 1881-1895), which concluded that the primary amino groups of the side chains in branched PEI are responsible for its much higher catalytic ester hydrolysis reactivity than the catalytic activity of linear PEI and poly(1-aminoethylene)(polyvinylamine).

To understand further the role of the enhanced rate of degradation when using a polyalkyleneimine crosslinking agent, 15 wt % hydrogels were prepared using the same crosslinker, $PEG_{3350}$-$(SSeb)_2$, and crosslinking agent, $PEI_{2000}$, but varying the PEG active ester to PEI primary amine ratio; the PEG active ester to PEI primary amine ratio was varied to 0.5:1, 0.75:1, or 1.15:1 (w/w). The hydrogels were prepared according to the table in FIG. 6A.

Figure 6:
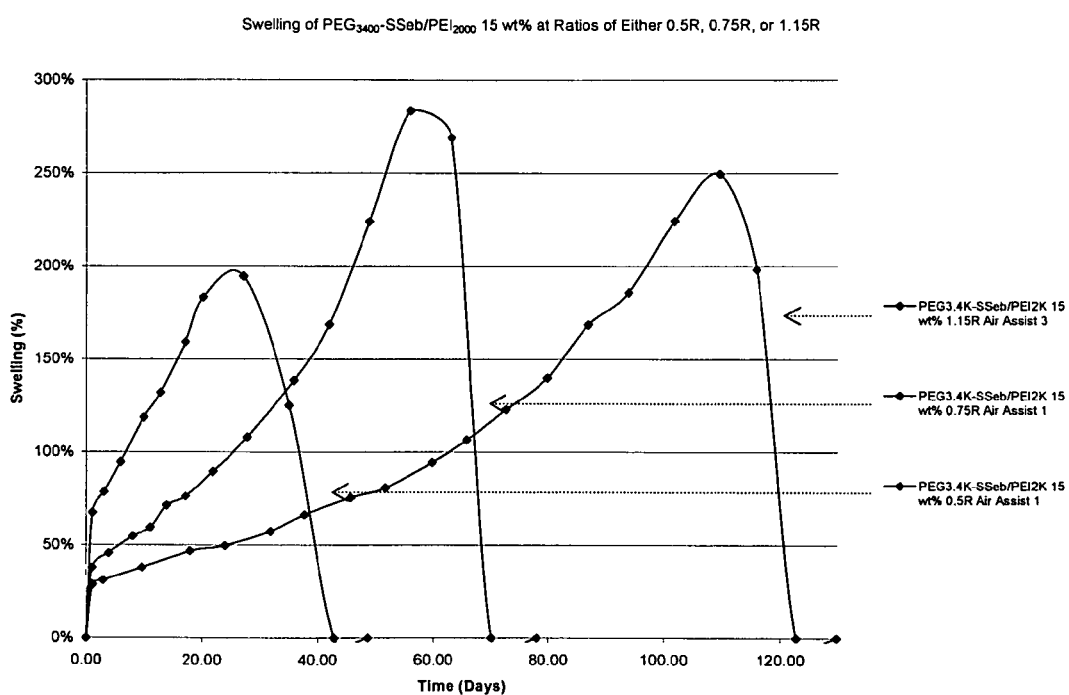
FIG. 6 depicts [A] a table showing the properties of hydrogels formed from different ratios of $PEG_{3350}$-$(SSeb)_2$ and $PEI_{2000}$; and [B] a graph showing the swelling of $PEG_{3350}$-$(SSeb)_2/PEI_{2000}$ at different ratios as a function of time.
Figure 16:
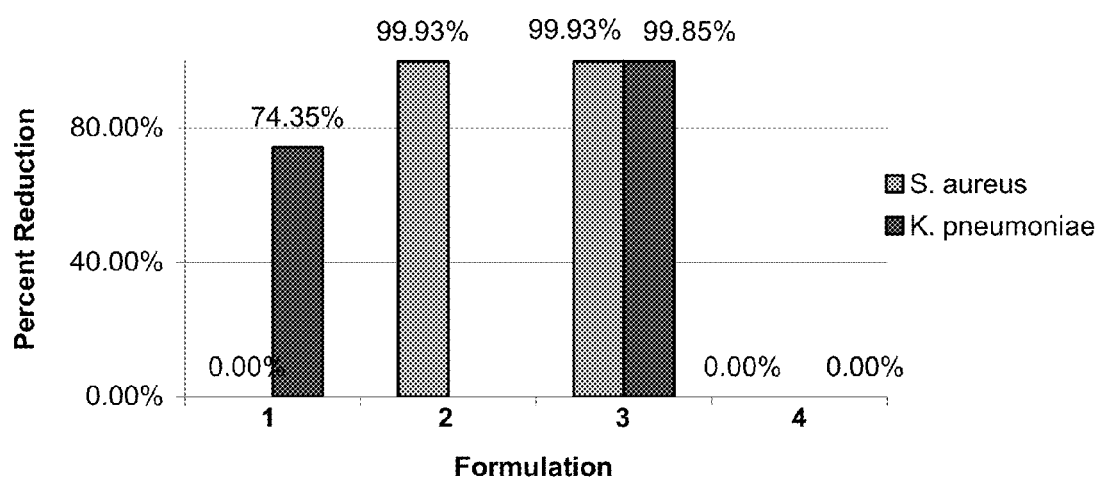
FIG. 16 depicts a chart summarizing the antimicrobial activity of formulations 1, 2, 3, and 4 after 24-hour contact time (AATCC Test Method 100) for two different organisms.

The hydrogels were placed in PBS at a pH of 7.4 and incubated at a temperature of 37° C. for the length of the study. The gels were gravimetrically monitored and the soaking solution was exchanged at least once per week. A summary of the gravimetric analysis is shown in FIG. 6B. Although there was a difference in equilibrium swelling, the rate of degradation, evidenced by a increase in swelling, decreases with a higher PEG active ester to PEI primary amine ratio.

The hydrogels were further monitored, after it became difficult/impossible to isolate the hydrogel, for time to visual degradation. The time to visual degradation is plotted in FIG. 7A. Overall, comparing a 0.5:1 (w/w) ratio to the 0.75:1 (w/w) ratio with a 33.3% decrease in the amount of PEI, the hydrogels were visually present approximately 60% longer. Furthermore, comparing a 0.75:1 (w/w) ratio to the 1.15:1 (w/w) ratio with a 34.7% decrease in the amount of PEI, the hydrogels were visually present approximately 65% longer. In sum, a decrease in PEG active ester to PEI primary amine ratio increases the concentration of PEI in the system, especially the number of free primary amines, which tends to systematically increase the rate of degradation, providing further evidence of polyalkyleneimines catalyzing the ester hydrolysis of the hydrogels.

Hydrogel swelling, at equilibrium, was also influenced by the composition of the crosslinking agent. $PEI_{2000}$ compositions typically swelled less than a comparative hydrogel with a Lys-Lys-Lys crosslinking agent (see FIG. 7B). This difference was not observed when the crosslinker $PEG_{3350}$-$(SG)_2$ was used, but the higher equilibrium swelling when using $PEI_{2000}$ may be attributed to significant degradation which has already occurred around 24 hours. Differences in swelling between the crosslinking agents may be related to the change in crosslink density imparted when using the hyperbranched polymer $PEI_{2000}$ with approximately 18 primary amines versus the trimer Lys-Lys-Lys with 4 primary amines.

Although the crosslink density of the compositions containing either $PEI_{2000}$ or Lys-Lys-Lys may be different, the crosslinking mechanism and crosslinkers were the same. The main difference between the crosslinking agents has to do with the number of carboxylic acids, primary, secondary, and tertiary amines (or their respective ions) on the crosslinking agent and the overall charge of the resulting hydrogel assuming complete reaction/crosslinking of the active groups. Although not intending to be bound by a particular theory, any differences in swelling and degradation may be attributed to the crosslink density and/or the increased spacing between the degradable ester functionality and the environment created by the presence of the polyalkyleneimine crosslinking agents.

Within the polyalkyleneimine crosslinking agents a trend can be observed whereby those with a larger number of crosslinking groups per molecule afford longer degradations times. Gels prepared using $PEG_{3350}$-$(SG)_2$ with either $PEI_{2000}$, $PEI_{1300}$, or PPI-DAB (G1), showed decreasing degradation times.

The table in FIG. 7C shows the swelling of gels prepared at 15 wt % with a series of polyamine base crosslinker which varied in the number of functional crosslinking groups. The swelling data was chosen at 40 hours as it was the last common time point before some of the gels had degraded. One can see the trend for quicker network degradation as the number of crosslinks per node decreases, i.e., when the primary amines per crosslinking molecule decreases.

With this degradation and equilibrium swelling data in mind, it is clear that certain crosslinkers should be used in combination with certain concentrations of polyalkyleneimines for specific hydrogel applications within the body. For instances hydrogels composed of $PEG_{3350}$-$(SS)_2$ or a derivative thereof could serve as temporary space fillers, scaffolds for other hydrogels or biocompatible materials, or other applications requiring a temporary hydrogel which will degrade almost immediately. Hydrogels composed of PEG$_{3350}$-(SG)$_2$ or a derivative thereof could be used in similar applications as PEG$_{3350}$-(SS)$_2$ or in instances where only approximately one day of useful mechanical life is needed or desired. This type of composition may be useful in cardiovascular applications or ophthalmic applications where wounds or lacerations have been known to re-endothelialize or re-epithelialize within 24 hours. Compositions composed of a PEG$_{3350}$-(succinimidyl adipate)$_2$ [PEG$_{3350}$-(SA)$_2$] crosslinker or a derivative thereof could be used when approximately one week of useful mechanical life is needed or desired. This type of composition may be useful in cardiovascular or pulmonary applications or for other incisions or wounds that typically heal in less than one week. Compositions composed of a PEG$_{3350}$-(SSeb)$_2$ crosslinker, or a longer carbon spacer chain, could be used when about three weeks or more of useful mechanical life is needed or desired. This type of composition may be useful in cardiovascular or pulmonary applications, neurosurgery, plastic surgery or for other incisions or wounds that typically heal on the order of weeks. Without the polyalkyleneimine crosslinking agent and the short spacing between the degradable ester functionality (i.e., m is 2 or 3; see FIG. 2), it seems the extremely quick degrading hydrogel compositions would not be possible. These examples also highlight the criticality of spacing the ester linkage farther from the polyalkyleneimine crosslinking agent (i.e., m is greater than 6 and m is greater than 7; see FIG. 2) in order to achieve a degradation time similar to other ester containing formulations that do not employ a polyalkyleneimine crosslinking agent. Moreover, the degradation rate within a certain carbon spacer length of the diacid can also be modified to achieve a broad range of degradation rates depending on the PEG:PEI ratio. Within certain ranges of PEG active ester to PEI primary amine ratios (approximately 0.75:1 to 1.3:1), the degradation rate may be modified significantly while minimally impacting swelling and mechanical properties.

It is conceived that there are other various linkages that could be examined such as activated polyalkylene glycol diacid derivatives composed of pimelic acid, suberic acid, azelaic acid, undecanedioic acid, dodecanedioic acid, 1,11-undecanedicarboxylic acid, tetradecanedioic acid, other diacids, or derivatives of these diacids.

The rate of degradation, the rate of ingrowth, and the mechanical strength of various embodiments of the invention were investigated and are discussed in Example 7.

Pharmaceutically Acceptable Salts

As set out herein, certain embodiments of the present materials may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. See, for example, *J. Pharm. Sci.* 1977, 66, 1-19.

The pharmaceutically acceptable salts of the subject compounds include the conventional nontoxic salts or ammonium salts of the compounds, e.g., from non-toxic organic or inorganic acids. For example, such as conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Biologically Active Agents and Pharmaceutically Active Agents

In certain embodiments, biologically active agents may be incorporated in the compositions of the invention. Active agents amenable for use in the compositions of the present invention include growth factors, such as transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are particularly preferred. Members of the TGF supergene family include the beta transforming growth factors (for example, TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB).

In addition to the biological active agents discussed above, a large number of pharmaceutical agents are known in the art and are amenable for use in the compositions of the invention. The term "pharmaceutical agent" includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Non-limiting examples of broad categories of useful pharmaceutical agents include the following therapeutic categories: anabolic agents, antacids, anti-asthmatic agents, anti-cholesterolemic and anti-lipid agents, anti-coagulants, anticonvulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and anti-thyroid agents, uterine relaxants, vitamins, and prodrugs.

More specifically, non-limiting examples of useful pharmaceutical agents include the following therapeutic categories: analgesics, such as nonsteroidal anti-inflammatory drugs, opiate agonists and salicylates; antihistamines, such as $H_1$-blockers and $H_2$-blockers; anti-infective agents, such as anthelmintics, antianaerobics, antibiotics, aminoglycoside antibiotics, antifungal antibiotics, cephalosporin antibiotics, macrolide antibiotics, miscellaneous beta-lactam antibiotics, penicillin antibiotics, quinolone antibiotics, sulfonamide antibiotics, tetracycline antibiotics, antimycobacterials, anti-tuberculosis antimycobacterials, antiprotozoals, antimalarial antiprotozoals, antiviral agents, anti-retroviral agents, scabicides, and urinary anti-infectives; antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor para-sympathomimetics, sympatholytics, alpha-blocker sympatholytics, beta-blocker sympatholytics, sympathomimetics, adrenergic agonist sympathomimetics; cardiovascular agents, such as antianginals, beta-blocker antianginals, calcium-channel blocker antianginals, nitrate antianginals, antiarrhythmics, cardiac glycoside antiarrhythmics, class I antiarrhythmics, class II antiarrhythmics, class III antiarrhythmics, class IV antiarrhythmics, antihypertensive agents, alpha-blocker antihypertensives, angiotensin-converting enzyme inhibitor (ACE inhibitor) antihypertensives, beta-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, HMG-CoA reductase inhibitor antilipemics, inotropes, cardiac glycoside inotropes, and thrombolytic agents; dermatological agents, such as antihistamines, anti-inflammatory agents, corticosteroid anti-inflammatory agents, antipruritics/local anesthetics, topical anti-infectives, antifungal topical anti-infectives, antiviral topical anti-infectives, and topical antineoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, $H_2$-blocker anti-ulcer agents, cholelitholytic agents, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, anti-androgens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immuno-suppressive anti-inflammatory agents, nonsteroidal anti-inflammatory drugs (NSAIDs), salicylate anti-inflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, such as anti-glaucoma agents, beta-blocker anti-glaucoma agents, miotic anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs (NSAIDs); psychotropic agents, such as antidepressants, heterocyclic antidepressants, monoamine oxidase inhibitors (MAOIs), selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti-inflammatory agents, and respiratory corticosteroid anti-inflammatory agents; toxicology agents, such as antidotes, heavy metal antagonists/chelating agents, substance abuse agents, deterrent substance abuse agents, and withdrawal substance abuse agents; minerals; and vitamins, such as vitamin A, vitamin B, vitamin C, vitamin D, vitamin E, and vitamin K.

Preferred classes of useful pharmaceutical agents from the above categories include: (1) nonsteroidal anti-inflammatory drugs (NSAIDs) analgesics, such as diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) $H_1$-blocker antihistamines, such as clemastine and terfenadine; (5) $H_2$-blocker antihistamines, such as cimetidine, famotidine, nizadine, and ranitidine; (6) anti-infective agents, such as mupirocin; (7) antianaerobic anti-infectives, such as chloramphenicol and clindamycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous beta-lactam antibiotic anti-infectives, such as aztreonam and imipenem; (11) penicillin antibiotic anti-infectives, such as nafcillin, oxacillin, penicillin G, and penicillin V; (12) quinolone antibiotic anti-infectives, such as ciprofloxacin and norfloxacin; (13) tetracycline antibiotic anti-infectives, such as doxycycline, minocycline, and tetracycline; (14) antituberculosis antimycobacterial anti-infectives such as isoniazid (INH), and rifampin; (15) antiprotozoal anti-infectives, such as atovaquone and dapsone; (16) antimalarial antiprotozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon alfa, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antimetabolite antineoplastic agents, such as fluorouracil (5-FU) and gemcitabine; (23) hormonal antineoplastics, such as goserelin, leuprolide, and tamoxifen; (24) natural antineoplastics, such as aldesleukin, interleukin-2, docetaxel, etoposide (VP-16), interferon alfa, paclitaxel, and tretinoin (ATRA); (25) antibiotic natural antineoplastics, such as bleomycin, dactinomycin, daunorubicin, doxorubicin, and mitomycin; (26) vinca alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) alpha-blocker sympatholytics, such as prazosin; (34) beta-blocker sympatholytics, such as atenolol; (35) adrenergic agonist sympathomimetics, such as albuterol and dobutamine; (36) cardiovascular agents, such as aspirin (ASA) (enteric coated ASA); (37) beta-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as digoxin; (41) class I antiarrhythmics, such as lidocaine, mexiletine, phenyloin, procainamide, and quinidine; (42) class II antiarrhythmics, such as atenolol, metoprolol, propranolol, and timolol; (43) class III antiarrhythmics, such as amiodarone; (44) class IV antiarrhythmics, such as diltiazem and verapamil; (45) α-blocker antihypertensives, such as prazosin; (46) angiotensin-converting enzyme inhibitor (ACE inhibitor) antihypertensives, such as captopril and enalapril; (47) β-blocker antihypertensives, such as atenolol, metoprolol, nadolol, and propanolol; (48) calcium-channel blocker antihypertensive agents, such as diltiazem and nifedipine; (49) central-acting adrenergic antihypertensives, such as clonidine and methyldopa; (50) diurectic antihypertensive agents, such as amiloride, furosemide, hydrochlorothiazide (HCTZ), and spironolactone; (51) peripheral vasodilator antihypertensives, such as hydralazine and minoxidil; (52) antilipemics, such as gemfibrozil and probucol; (53) bile acid sequestrant antilipemics, such as cholestyramine; (54) HMG-CoA reductase inhibitor antilipemics, such as lovastatin and pravastatin; (55) inotropes, such as amrinone, dobutamine, and dopamine; (56) cardiac glycoside inotropes, such as digoxin; (57) thrombolytic agents, such as alteplase (TPA), anistreplase, streptokinase, and urokinase; (58) dermatological agents, such as colchicine, isotretinoin, methotrexate, minoxidil, tretinoin (ATRA); (59) dermatological corticosteroid anti-inflammatory agents, such as betamethasone and dexamethasone; (60) antifungal topical anti-infectives, such as amphotericin B, clotrimazole, miconazole, and nystatin; (61) antiviral topical anti-infectives, such as acyclovir; (62) topical antineoplastics, such as fluorouracil (5-FU); (63) electrolytic and renal agents, such as lactulose; (64) loop diuretics, such as furosemide; (65) potassium-sparing diuretics, such as triamterene; (66) thiazide diuretics, such as hydro-chlorothiazide (HCTZ); (67) uricosuric agents, such as probenecid; (68) enzymes such as RNase and DNase; (69) thrombolytic enzymes, such as alteplase, anistreplase, streptokinase and urokinase; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) $H_2$-blocker anti-ulcer agents, such as cimetidine, famotidine, nizatidine, and ranitidine; (74) digestants, such as pancrelipase; (75) prokinetic agents, such as erythromycin; (76) opiate agonist intravenous anesthetics such as fentanyl; (77) hematopoietic antianemia agents, such as erythropoietin, filgrastim (G-CSF), and sargramostim (GM-CSF); (78) coagulation agents, such as anti-hemophilic factors 1-10 (AHF 1-10); (79) anticoagulants, such as warfarin; (80) thrombolytic enzyme coagulation agents, such as alteplase, anistreplase, streptokinase and urokinase; (81) hormones and hormone modifiers, such as bromocriptine; (82) abortifacients, such as methotrexate; (83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadatropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-1b and interferon gamma-1b; (93) immunoglobulins, such as immune globulin IM, IMIG, IGIM and immune globulin IV, IVIG, IGIV; (94) amide local anesthetics, such as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs (NSAIDs), such as diclofenac, ibuprofen, ketoprofen, ketorlac, and naproxen; (99) skeletal muscle relaxants, such as baclofen, cyclobenzaprine, and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenyloin, and valproic acid; (103) barbiturate anticonvulsants, such as phenobarbital and primidone; (104) benzodiazepine anticonvulsants, such as clonazepam, diazepam, and lorazepam; (105) anti-parkisonian agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) β-blocker anti-glaucoma agents, such as timolol; (110) miotic anti-glaucoma agents, such as pilocarpine; (111) ophthalmic aminoglycoside antiinfectives, such as gentamicin, neomycin, and tobramycin; (112) ophthalmic quinolone anti-infectives, such as ciprofloxacin, norfloxacin, and ofloxacin; (113) ophthalmic corticosteroid anti-inflammatory agents, such as dexamethasone and prednisolone; (114) ophthalmic nonsteroidal anti-inflammatory drugs (NSAIDs), such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) antitussives, such as codeine; (119) bronchodilators, such as theophylline; (120) adrenergic agonist bronchodilators, such as albuterol; (121) respiratory corticosteroid anti-inflammatory agents, such as dexamethasone; (122) antidotes, such as flumazenil and naloxone; (123) heavy metal antagonists/chelating agents, such as penicillamine; (124) deterrent substance abuse agents, such as disulfuram, naltrexone, and nicotine; (125) withdrawal substance abuse agents, such as bromocriptine; (126) minerals, such as iron, calcium, and magnesium; (127) vitamin B compounds, such as cyanocobalamin (vitamin B12) and niacin (vitamin B3); (128) vitamin C compounds, such as ascorbic acid; and (129) vitamin D compounds, such as calcitriol.

In addition to the foregoing, the following less common drugs may also be used: chlorhexidine; estradiol cypionate in oil; estradiol valerate in oil; flurbiprofen; flurbiprofen sodium; ivermectin; levodopa; nafarelin; and somatropin. Further, the following drugs may also be used: recombinant beta-glucan; bovine immunoglobulin concentrate; bovine superoxide dismutase; the formulation comprising fluorouracil, epinephrine, and bovine collagen; recombinant hirudin (r-Hir), HIV-1 immunogen; human anti-TAC antibody; recombinant human growth hormone (r-hGH); recombinant human hemoglobin (r-Hb); recombinant human mecasermin (r-IGF-1); recombinant interferon β-1a; lenograstim (G-CSF); olanzapine; recombinant thyroid stimulating hormone (r-TSH); and topotecan.

Further still, the following intravenous products may be used: acyclovir sodium; aldesleukin; atenolol; bleomycin sulfate, human calcitonin; salmon calcitonin; carboplatin; carmustine; dactinomycin, daunorubicin HCl; docetaxel; doxorubicin HCl; epoetin alfa; etoposide (VP-16); fluorouracil (5-FU); ganciclovir sodium; gentamicin sulfate; interferon alfa; leuprolide acetate; meperidine HCl; methadone HCl; methotrexate sodium; paclitaxel; ranitidine HCl; vinblastin sulfate; and zidovudine (AZT).

Further specific examples of useful pharmaceutical agents from the above categories include: (a) anti-neoplastics such as androgen inhibitors, antimetabolites, cytotoxic agents, and immunomodulators; (b) anti-tussives such as dextromethorphan, dextromethorphan hydrobromide, noscapine, carbetapentane citrate, and chlorphedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate and morphine; (f) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines, and other bioactive peptidic compounds, such as interleukins 1-18 including mutants and analogues, RNase, DNase, luteinizing hormone releasing hormone (LHRH) and analogues, gonadotropin releasing hormone (GnRH), transforming growth factor-.beta. (TGF-beta), fibroblast growth factor (FGF), tumor necrosis factor-alpha & beta (TNF-alpha & beta), nerve growth factor (NGF), growth hormone releasing factor (GHRF), epidermal growth factor (EGF), fibroblast growth factor homologous factor (FGFHF), hepatocyte growth factor (HGF), insulin growth factor (IGF), invasion inhibiting factor-2 (IIF-2), bone morphogenetic proteins 1-7 (BMP 1-7), somatostatin, thymosin-alpha-1, gamma-globulin, superoxide dismutase (SOD), complement factors, hGH, tPA, calcitonin, ANF, EPO and insulin; and (n) anti-infective agents such as antifungals, anti-virals, antiseptics and antibiotics.

Alternatively, the pharmaceutical agent may be a radiosensitizer, such as metoclopramide, sensamide or neusensamide (manufactured by Oxigene); profiromycin (made by Vion); RSR13 (made by Allos); Thymitaq (made by Agouron), etanidazole or lobenguane (manufactured by Nycomed); gadolinium texaphrin (made by Pharmacyclics); BuDR/Broxine (made by NeoPharm); IPdR (made by Sparta); CR2412 (made by Cell Therapeutic); L1X (made by Terrapin); or the like. Preferably, the biologically active substance is selected from the group consisting of peptides, poly-peptides, proteins, amino acids, polysaccharides, growth factors, hormones, anti-angiogenesis factors, interferons or cytokines, and pro-drugs. In a particularly preferred embodiment, the biologically active substance is a therapeutic drug or pro-drug, most preferably a drug selected from the group consisting of chemotherapeutic agents and other anti-neoplastics such as paclitaxel, antibiotics, anti-virals, antifungals, anti-inflammatories, and anticoagulants.

The biologically active substances are used in amounts that are therapeutically effective. While the effective amount of a biologically active substance will depend on the particular material being used, amounts of the biologically active substance from about 1% to about 65% may be desirable. Lesser amounts may be used to achieve efficacious levels of treatment for certain biologically active substances.

Selected Examples of Other Additives

The compositions of the invention may also be mixed with natural polymers such as collagen, hyaluronic acid, gelatin, heparin, fibrin and/or heparan sulfate. In certain embodiments, a synthetic or natural polymer which may or may not be involved in the crosslinking reaction is added either before, during, and/or after mixing of the polyalkyleneimine and the polymerization agent. The synthetic or natural polymers can enhance the mechanical properties, affect adhesion, alter the degradation rates, alter viscosity, and/or provide signaling to specific cells. Representative examples of natural polymers which can be added to the compositions of the invention include collagen, hyaluronic acid, albumin, cellulose, elastin, fibrin, fibronectin, polylysine, and RGD-containing peptides. Examples of synthetic polymers include poly(vinyl acetate), polyvinylpyrrolidone, poly(acrylic acid), poly(ethylene glycol), poly(propylene glycol)-poly(ethylene glycol) copolymer, and trimethylene carbonate. The synthetic or natural polymers to be added can be soluble in aqueous solution or can be insoluble in aqueous solution and dispersed throughout the compositions of the invention to create a composite material.

In certain embodiments, a polyalkylene glycol containing nucleophilic groups is added to the polyalkyleneimine prior to mixing the polyalkyleneimine with a polyalkylene glycol containing electrophilic groups. In certain embodiments, a PEG is modified to contain amine groups and/or thiol groups. The modified PEG is mixed with the polyalkyleneimine, and then the polyalkyleneimine/modified-PEG solution is added to the PEG-electrophile solution to form the hydrogel. Incorporation of this third active component into the hydrogel can affect hydrogel properties. For example, the resultant hydrogel may swell more, be less mechanically strong, and/or degrade faster compared to a hydrogel prepared without a PEG containing nucleophilic groups.

In certain embodiments, a polyalkylene glycol containing nucleophilic groups is added to the polyalkyleneimine containing electrophilic groups. In certain embodiments, the polyalkylene glycol contains amino and/or thiol groups. In certain embodiments, the polyalkyleneimine contains an N-hydroxysuccinimide group optionally substituted with a sulfonic acid group.

In certain embodiments, the hydrogel formed by reaction of a polyalkyleneimine and a polymerization agent is treated with an acrylate to form a photo-polymerization agent. Then, the photo-polymerization agent is treated with visible or ultra-violet light sufficient to polymerize the photo-polymerization agent.

In certain embodiments, a polyalkyleneimine containing a plurality of photopolymerizable groups, optionally in the presence of a polyalkylene glycol containing a plurality of photopolymerizable groups, is treated with visible light or ultraviolet light sufficient to polyermize the polyalkyleneimine. In certain embodiments, the photopolymerizable group is an acrylate, such as methacrylate. In certain instances when visible light is used to polymerize the polyalkyleneimine, a photoinitiator is admixed with the polyalkyleneimine. A large number of photoinitiators are known in the art and are amenable to the present invention. For example, eosin y is a photoinitiator that may be used with the polyalkyleneimines described herein.

Sterilization Procedures

A variety of procedures are known in the art for sterilizing a chemical composition. Sterilization may be accomplished by chemical, physical, or irradiation techniques. Examples of chemical methods include exposure to ethylene oxide or hydrogen peroxide vapor. Examples of physical methods include sterilization by heat (dry or moist), retort canning, and filtration. The British Pharmacopoeia recommends heating at a minimum of 160° C. for not less than 2 hours, a minimum of 170° C. for not less than 1 hour and a minimum of 180° C. for not less than 30 minutes for effective sterilization. For examples of heat sterilization, see U.S. Pat. No. 6,136,326, which is hereby incorporated by reference. Passing the chemical composition through a membrane can be used to sterilize a composition. For example, the composition is filtered through a small pore filter such as a 0.22 micron filter which comprises material inert to the composition being filtered. In certain embodiments, the filtration is conducted in a Class 100,000 or better clean room. Examples of irradiation methods include gamma irradiation, electron beam irradiation, microwave irradiation, and irradiation using visible light. One preferred method is electron beam irradiation, as described in U.S. Pat. Nos. 6,743,858; 6,248,800; and 6,143,805, each of which is hereby incorporated by reference.

There are several sources for electron beam irradiation. The two main groups of electron beam accelerators are: (1) a Dynamitron, which uses an insulated core transformer, and (2) radio frequency (RF) linear accelerators (linacs). The Dynamitron is a particle accelerator (4.5 MeV) designed to impart energy to electrons. The high energy electrons are generated and accelerated by the electrostatic fields of the accelerator electrodes arranged within the length of the glass-insulated beam tube (acceleration tube). These electrons, traveling through an extension of the evacuation beam tube and beam transport (drift pipe) are subjected to a magnet deflection system in order to produce a "scanned" beam, prior to leaving the vacuum enclosure through a beam window. The dose can be adjusted with the control of the percent scan, the beam current, and the conveyor speed. In certain embodiments, the electron-beam radiation employed may be maintained at an initial fluence of at least about 2 $\mu Curie/cm^2$, at least about 5 $\mu Curie/cm^2$, at least about 8 $\mu Curie/cm^2$, or at least about 10 $\mu Curie/cm^2$. In certain embodiments, the electron-beam radiation employed has an initial fluence of from about 2 to about 25 $\mu Curie/cm^2$. In certain embodiments, the electron-beam dosage is from about 5 to 50 kGray, or from about 15 to about 20 kGray with the specific dosage being selected relative to the density of material being subjected to electron-beam radiation as well as the amount of bioburden estimated to be therein. Such factors are well within the skill of the art.

The composition to be sterilized may be in any type of at least partially electron beam permeable container such as glass or plastic. In embodiments of the present invention, the container may be sealed or have an opening. Examples of glass containers include ampuoles, vials, syringes, pipettes, applicators, and the like. The penetration of electron beam irradiation is a function of the packaging. If there is not enough penetration from the side of a stationary electron beam, the container may be flipped or rotated to achieve adequate penetration. Alternatively, the electron beam source can be moved about a stationary package. In order to determine the dose distribution and dose penetration in product load, a dose map can be performed. This will identify the minimum and maximum dose zone within a product.

Procedures for sterilization using visible light are described in U.S. Pat. No. 6,579,916, which is hereby incorporated by reference. The visible light for sterilization can be generated using any conventional generator of sufficient power and breadth of wavelength to effect sterilization. Generators are commercially available under the tradename PureBright® in-line sterilization systems from PurePulse Technologies, Inc. 4241 Ponderosa Ave, San Diego, Calif. 92123, USA. The PureBright® in-line sterilization system employs visible light to sterilize clear liquids at an intensity approximately 90,000 times greater than surface sunlight. If the amount of UV light penetration is of concern, conventional UV absorbing materials can be used to filter out the UV light.

In certain embodiments, the composition is sterilized to provide a Sterility Assurance Level (SAL) of at least about $10^{-3}$. The Sterility Assurance Level measurement standard is described, for example, in ISO/CD 14937, the entire disclosure of which is incorporated herein by reference. In certain embodiments, the Sterility Assurance Level may be at least about $10^{-4}$, at least about $10^{-5}$, or at least about $10^{-6}$.

In certain embodiments of the present invention, one or more of the compositions, reagents, or components of a kit has been sterilized. The sterilization may be achieved using gamma radiation, e-beam radiation, dry heat sterilization, ethylene oxide sterilization, or a combination of any of them. The compositions, reagents, or components of the kits can be sterilized in an aqueous solution or neat.

In certain embodiments, the present invention relates to the aforementioned method, wherein said sterilizing is performed by treatment with ethylene oxide, hydrogen peroxide, heat, gamma irradiation, electron beam irradiation, microwave irradiation, or visible light irradiation.

Delivery Systems

The composition of the present invention may be delivered, for example, to the wound, void, or damaged tissue of a patient using a large number of known delivery devices. For example, the delivery system may be a single-barrel syringe system. In certain embodiments, the single-barrel syringe is a double acting, single-barrel syringe system. In certain situations, a double- or multi-barrel syringe system may be preferable. In instances where the polymerizable polyalkyleneimine is mixed with a polymerization agent prior to delivering the solution to a patient, a delivery device that flows two or more streams of liquid in a mixing chamber may be preferable. Alternatively, a delivery device that mixes two solids and two liquids and then separately flows these streams of liquid to a mixing chamber may be advantageous. In certain embodiments, delivery may be assisted with machines, compressed air or gases, and the like. Of course, variations may be made in the size of the delivery device, the length of the delivery device, and/or the use of machines to aid in delivery.

In certain embodiments, a delivery system is used to deliver the materials to a patient, wherein at least two dry, reactive components are stored together in a dry state and introduced into a liquid component(s) at the time of use to form a mixture that forms a hydrogel.

In certain embodiments, it may be advantageous to mix the components used to form the hydrogel by static mixing device such as a tortuous path mixing element. As an example, both components could be dissolved in aqueous solution prior to use. Once mixed, the solutions would polymerize in a predetermined amount of time.

Another aspect of the invention relates to a method of preparing a hydrogel, comprising the steps of combining an aqueous solution of a first component, and a neat form of a second component to give a mixture; and applying the mixture to a tissue site. In certain embodiments, the present invention relates to the aforementioned method, wherein said step of combining to give said mixture occurs shortly before said step of applying. In certain embodiments, the present invention relates to the aforementioned method, wherein said step of combining to give said mixture occurs less than about 30 minutes before said step of applying. In certain embodiments, the present invention relates to the aforementioned method, wherein said step of combining to give said mixture occurs less than about 20 minutes before said step of applying. In certain embodiments, the present invention relates to the aforementioned method, wherein said step of combining to give said mixture occurs less than about 10 minutes before said step of applying. In certain embodiments, the present invention relates to the aforementioned method, wherein said step of combining to give said mixture occurs less than about 5 minutes before said step of applying.

Another aspect of the invention relates to a method of controlling the polymerization of a two component hydrogel system through combining the two components in an aqueous solution in one container with a final solution pH in a range unsuitable for crosslinking, and expressing the solution through an ion exchange resin to either lower or raise the pH of the solution to a range suitable for crosslinking. For example, the two components could be mixed (without gelation) prior to applying the mixture to a patient. The pH of the mixing solution may be adjusted in order to slow or prevent crosslinking of hydrogel components. Once the components used to form the hydrogel are mixed, the resultant solution may be contacted with a frit or resin designed to raise or lower the pH to a level suitable for crosslinking.

Another aspect of the invention relates to a method of controlling the polymerization of a two component hydrogel system through combining an aqueous solution of the first component with a neat form of the second component with a final solution pH in a range unsuitable for crosslinking, and expressing the solution through an ion exchange resin to either lower or raise the pH of the solution to a range suitable for crosslinking.

For example, PEG-NHS and a PEI could be mixed during packaging and dissolved prior to use in a buffer designed to provide a solution with a pH of about 6. The solution is mixed, and then the solution is contacted with a resin embedded in the delivery device. The resin would raise the pH to about 7 or 8 for initiate crosslinking.

Another aspect of the invention relates to one the methods described herein for sealing a wound, void, or damaged tissue wherein the components are PEG-NHS and $PEI_{2000}$, the initial pH of the solution containing the combined components is below approximately pH 7, and the ion exchange resin is an anion exchange resin (including but not limited to MTO-Dowex M43, Dowex 66, or Dowex 1X2-200).

Another aspect of the invention relates to a method of controlling the polymerization of a two component hydrogel system through combining the two components in an aqueous solution in one container with a final solution pH in a range unsuitable for crosslinking, and expressing the solution through an frit/resin coated/loaded with an acidic or basic media to lower or raise the pH of the solution to a range suitable for crosslinking.

Another aspect of the invention relates to a method of controlling the polymerization of a two component hydrogel system through combining the two components in an aqueous solution in one container with a final solution pH in a range unsuitable for crosslinking, and contacting the solution with an applicator loaded with either an acidic or basic media to lower or raise the pH of the solution to a range suitable for crosslinking.

The above methods may be optimized by modifying, inter alia, the size and shape of the instrument that that delivers the solution suitable for crosslinking. For example, the diameter and/or length of the crosslinking-solution holding chamber can be altered, or the diameter and/or length of the chamber housing the frit/resin loaded with an acidic or basic media can be altered. Similarly, the applicator tip of the delivery instrument can be permanent or disposable. The delivery instrument may be constructed so that the crosslinking solution is applied as a spray, mist, or liquid. In certain embodiments, the delivery instrument is a single or double barrel syringe. Further, it is appreciated that the above methods may involve gas-assisted delivery of the crosslinking solution. In certain embodiments, the above methods may employ a brush or sponge to delivery the hydrogel to the tissue.

Selected Compositions and Methods of the Invention

One aspect of the invention relates to a polymeric composition in contact with tissue, comprising an activated polyalkylene glycol diacid derivative and a crosslinking agent; wherein the activated polyalkylene glycol diacid derivative is represented by formula I:

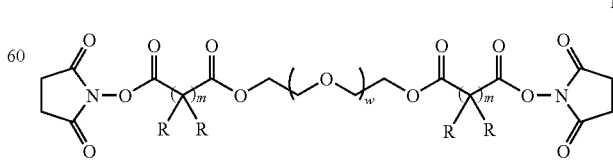

I wherein, independently for each occurrence, R is H or lower alkyl; m is 2-20 inclusive; and w is 5 to 1,000 inclusive.

In certain embodiments, the invention relates to an aforementioned composition, wherein the crosslinking agent is a polyalkyleneimine or trilysine. In certain embodiments, the invention relates to an aforementioned composition, wherein the crosslinking agent is a polyethyleneimine (PEI). In certain embodiments, the invention relates to an aforementioned composition, wherein the crosslinking agent is $PEI_{25000}$, $PEI_{5000}$, $PEI_{2000}$, $PEI_{1300}$, $PEI_{800}$, or a PEI-based or PPI-based dendritic structure. In certain embodiments, the invention relates to an aforementioned composition, wherein the crosslinking agent is $PEI_{2000}$. In certain embodiments, the invention relates to an aforementioned composition, wherein the crosslinking agent is trilysine.

In certain embodiments, the invention relates to an aforementioned composition, wherein m is 5-20 inclusive. In certain embodiments, the invention relates to an aforementioned composition, wherein m is 5-10 inclusive. In certain embodiments, the invention relates to an aforementioned composition, wherein m is 2-10 inclusive. In certain embodiments, the invention relates to an aforementioned composition, wherein m is 2. In certain embodiments, the invention relates to an aforementioned composition, wherein m is 3. In certain embodiments, the invention relates to an aforementioned composition, wherein m is 4. In certain embodiments, the invention relates to an aforementioned composition, wherein m is 5. In certain embodiments, the invention relates to an aforementioned composition, wherein m is 6. In certain embodiments, the invention relates to an aforementioned composition, wherein m is 7. In certain embodiments, the invention relates to an aforementioned composition, wherein m is 8. In certain embodiments, the invention relates to an aforementioned composition, wherein m is 9. In certain embodiments, the invention relates to an aforementioned composition, wherein m is 10. In certain embodiments, the invention relates to an aforementioned composition, wherein m is 11. In certain embodiments, the invention relates to an aforementioned composition, wherein m is 12. In certain embodiments, the invention relates to an aforementioned composition, wherein m is 13.

In certain embodiments, the invention relates to an aforementioned composition, wherein w is 5 to 20 inclusive. In certain embodiments, the invention relates to an aforementioned composition, wherein w is 20 to 120 inclusive. In certain embodiments, the invention relates to an aforementioned composition, wherein w is 120 to 250 inclusive.

In certain embodiments, the invention relates to an aforementioned composition, wherein the activated polyalkylene glycol diacid derivative is $R\text{-}PEG_n\text{-}R$; wherein n represents the number average molecular weight of the PEG and is about 2000 to about 12,000 inclusive; and R is SS, SG, SA, SSub, or SSeb. In certain embodiments, the invention relates to an aforementioned composition, wherein the activated polyalkylene glycol diacid derivative is $R\text{-}PEG_n\text{-}R$; wherein n represents the number average molecular weight of the PEG and is 3350, 4600, 6000, 8000, or 10000; and R is SS, SG, SA, SSub, or SSeb. In certain embodiments, the invention relates to an aforementioned composition, wherein the activated polyalkylene glycol diacid derivative is $PEG_{3350}\text{-}(SS)_2$. In certain embodiments, the invention relates to an aforementioned composition, wherein the activated polyalkylene glycol diacid derivative is $PEG_{3350}\text{-}(SG)_2$. In certain embodiments, the invention relates to an aforementioned composition, wherein the activated polyalkylene glycol diacid derivative is $PEG_{3350}\text{-}(SA)_2$. In certain embodiments, the invention relates to an aforementioned composition, wherein the activated polyalkylene glycol diacid derivative is $PEG_{3350}\text{-}(SSeb)_2$. In certain embodiments, the invention relates to an aforementioned composition, wherein the activated polyalkylene glycol diacid derivative is $PEG_{3350}\text{-}(SSub)_2$.

In certain embodiments, the invention relates to an aforementioned composition, wherein the weight percent crosslinker is between about 5% and about 50%. In certain embodiments, the invention relates to an aforementioned composition, wherein the weight percent crosslinker is between about 5% and about 20%. In certain embodiments, the invention relates to an aforementioned composition, wherein the weight percent crosslinker is about 15%.

In certain embodiments, the invention relates to an aforementioned composition, wherein the ratio of activated esters on the polyalkylene glycol diacid derivatives to primary amines on the crosslinking agent is in the range from about 0.10:1 to about 10:1. In certain embodiments, the invention relates to an aforementioned composition, wherein the ratio of activated esters on the polyalkylene glycol diacid derivatives to primary amines on the crosslinking agent is in the range from about 0.50:1 to about 1.5:1. In certain embodiments, the invention relates to an aforementioned composition, wherein the ratio of activated esters on the polyalkylene glycol diacid derivatives to primary amines on the crosslinking agent is in the range from about 0.75:1 to about 1.3:1.

In certain embodiments, the invention relates to an aforementioned composition, wherein the ratio (w/w) of activated polyalkylene glycol diacid derivative to crosslinking agent is about 2:1 to 10:1. In certain embodiments, the invention relates to an aforementioned composition, wherein the ratio (w/w) of activated polyalkylene glycol diacid derivative to crosslinking agent is about 11:1 to 20:1. In certain embodiments, the invention relates to an aforementioned composition, wherein the ratio (w/w) of activated polyalkylene glycol diacid derivative to crosslinking agent is about 21:1 to 30:1. In certain embodiments, the invention relates to an aforementioned composition, wherein the ratio (w/w) of activated polyalkylene glycol diacid derivative to crosslinking agent is about 31:1 to 40:1. In certain embodiments, the invention relates to an aforementioned composition, wherein the ratio (w/w) of activated polyalkylene glycol diacid derivative to crosslinking agent is about 41:1 to 50:1. In certain embodiments, the invention relates to an aforementioned composition, wherein the ratio (w/w) of activated polyalkylene glycol diacid derivative to crosslinking agent is about 51:1 to 60:1. In certain embodiments, the invention relates to an aforementioned composition, wherein the ratio (w/w) of activated polyalkylene glycol diacid derivative to crosslinking agent is about 61:1 to 70:1.

One aspect of the invention relates to a method of sealing a wound of a patient, comprising the steps of: combining effective amounts of an activated polyalkylene glycol diacid derivative and a crosslinking agent to form a composition, and applying said composition to a wound of a patient; wherein the activated polyalkylene glycol diacid derivative is represented by formula I:

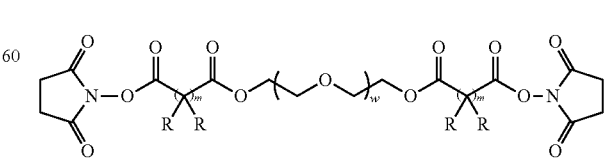

wherein, independently for each occurrence, R is H or lower alkyl; m is 2-20 inclusive; and w is to 1,000 inclusive.

One aspect of the invention relates to a method of augmenting soft tissue or filling a void of a patient, comprising the steps of: combining effective amounts of an activated polyalkylene glycol diacid derivative and a crosslinking agent to form a composition, and applying said composition to soft tissue or a void of a patient; wherein the activated polyalkylene glycol diacid derivative is represented by formula I:

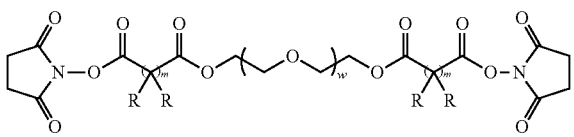

wherein, independently for each occurrence, R is H or lower alkyl; m is 2-20 inclusive; and w is 5 to 1,000 inclusive.

One aspect of the invention relates to a method of adhering tissues of a patient, comprising the steps of: combining effective amounts of an activated polyalkylene glycol diacid derivative and a crosslinking agent to form a composition, applying said composition to a first tissue of a patient to form a modified tissue, and contacting said modified tissue with a second tissue of a patient; wherein the activated polyalkylene glycol diacid derivative is represented by formula I:

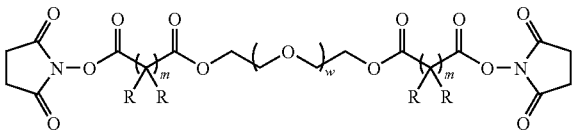

wherein, independently for each occurrence, R is H or lower alkyl; m is 2-20 inclusive; and w is 5 to 1,000 inclusive.

One aspect of the invention relates to a method of securing a prosthetic material to the tissues of a patient, comprising the steps of: combining effective amounts of an activated polyalkylene glycol diacid derivative and a crosslinking agent to form a composition; applying said composition to the prosthetic material, thereby forming a modified prosthetic material; contacting the modified prosthetic material to the tissues of the patient, thereby securing the prosthetic material to the tissues of the patient; wherein the activated polyalkylene glycol diacid derivative is represented by formula I:

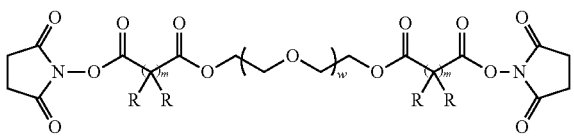

wherein, independently for each occurrence, R is H or lower alkyl; m is 2-20 inclusive; and w is 5 to 1,000 inclusive.

One aspect of the invention relates to a method of substantially minimizing a microbial population, comprising the steps of: combining effective amounts of an activated polyalkylene glycol diacid derivative and a crosslinking agent to form a composition; applying said composition to the microbial population, wherein the activated polyalkylene glycol diacid derivative is represented by formula I:

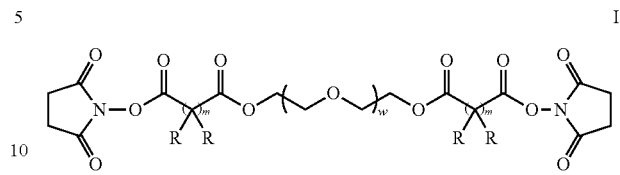

wherein, independently for each occurrence, R is H or lower alkyl; m is 2-20 inclusive; and w is 5 to 1,000 inclusive.

In certain embodiments, the invention relates to an aforementioned method, wherein the crosslinking agent is a polyalkyleneimine or trilysine. In certain embodiments, the invention relates to an aforementioned method, wherein the crosslinking agent is a polyethyleneimine (PEI). In certain embodiments, the invention relates to an aforementioned method, wherein the crosslinking agent is $PEI_{25000}$, $PEI_{5000}$, $PEI_{2000}$, $PEI_{1300}$, $PEI_{800}$, or a PEI-based or PPI-based dendritic structure. In certain embodiments, the invention relates to an aforementioned method, wherein the crosslinking agent is $PEI_{2000}$. In certain embodiments, the invention relates to an aforementioned method, wherein the crosslinking agent is trilysine.

In certain embodiments, the invention relates to an aforementioned method, wherein m is 5-20 inclusive. In certain embodiments, the invention relates to an aforementioned method, wherein m is 5-10 inclusive. In certain embodiments, the invention relates to an aforementioned method, wherein m is 2-10 inclusive. In certain embodiments, the invention relates to an aforementioned method, wherein m is 2. In certain embodiments, the invention relates to an aforementioned method, wherein m is 3. In certain embodiments, the invention relates to an aforementioned method, wherein m is 4. In certain embodiments, the invention relates to an aforementioned method, wherein m is 5. In certain embodiments, the invention relates to an aforementioned method, wherein m is 6. In certain embodiments, the invention relates to an aforementioned method, wherein m is 7. In certain embodiments, the invention relates to an aforementioned method, wherein m is 8. In certain embodiments, the invention relates to an aforementioned method, wherein m is 9. In certain embodiments, the invention relates to an aforementioned method, wherein m is 10. In certain embodiments, the invention relates to an aforementioned method, wherein m is 11. In certain embodiments, the invention relates to an aforementioned method, wherein m is 12. In certain embodiments, the invention relates to an aforementioned method, wherein m is 13.

In certain embodiments, the invention relates to an aforementioned method, wherein w is 5 to 20 inclusive. In certain embodiments, the invention relates to an aforementioned method, wherein w is 20 to 120 inclusive. In certain embodiments, the invention relates to an aforementioned method, wherein w is 120 to 250 inclusive.

In certain embodiments, the invention relates to an aforementioned method, wherein the activated polyalkylene glycol diacid derivative is $R\text{-}PEG_n\text{-}R$; wherein n represents the number average molecular weight of the PEG and is about 2000 to about 12,000 inclusive; and R is SS, SG, SA, SSub, or SSeb. In certain embodiments, the invention relates to an aforementioned method, wherein the activated polyalkylene glycol diacid derivative is $R\text{-}PEG_n\text{-}R$; wherein n represents the number average molecular weight of the PEG and n is 3350, 4600, 6000, 8000, or 10000; and R is SS, SG, SA, SSub, or SSeb. In certain embodiments, the invention relates to an aforementioned method, wherein the activated polyalkylene glycol diacid derivative is $PEG_{3350}$-$(SS)_2$. In certain embodiments, the invention relates to an aforementioned method, wherein the activated polyalkylene glycol diacid derivative is $PEG_{3350}$-$(SG)_2$. In certain embodiments, the invention relates to an aforementioned method, wherein the activated polyalkylene glycol diacid derivative is $PEG_{3350}$-$(SA)_2$. In certain embodiments, the invention relates to an aforementioned method, wherein the activated polyalkylene glycol diacid derivative is $PEG_{3350}$-$(SSeb)_2$.

In certain embodiments, the invention relates to an aforementioned method, wherein the weight percent crosslinker is between about 5% and about 50%. In certain embodiments, the invention relates to an aforementioned method, wherein the weight percent crosslinker is between about 5% and about 20%. In certain embodiments, the invention relates to an aforementioned method, wherein the weight percent crosslinker is about 15%.

In certain embodiments, the invention relates to an aforementioned method, wherein the ratio of activated esters on the polyalkylene glycol diacid derivatives to primary amines on the crosslinking agent is in the range from about 0.10:1 to about 10:1. In certain embodiments, the invention relates to an aforementioned method, wherein the ratio of activated esters on the polyalkylene glycol diacid derivatives to primary amines on the crosslinking agent is in the range from about 0.50:1 to about 1.5:1. In certain embodiments, the invention relates to an aforementioned method, wherein the ratio of activated esters on the polyalkylene glycol diacid derivatives to primary amines on the crosslinking agent is in the range from about 0.75:1 to about 1.3:1.

In certain embodiments, the invention relates to an aforementioned method, wherein the ratio (w/w) of activated polyalkylene glycol diacid derivative to crosslinking agent is about 2:1 to 10:1. In certain embodiments, the invention relates to an aforementioned method, wherein the ratio (w/w) of activated polyalkylene glycol diacid derivative to crosslinking agent is about 11:1 to 20:1. In certain embodiments, the invention relates to an aforementioned method, wherein the ratio (w/w) of activated polyalkylene glycol diacid derivative to crosslinking agent is about 21:1 to 30:1. In certain embodiments, the invention relates to an aforementioned method, wherein the ratio (w/w) of activated polyalkylene glycol diacid derivative to crosslinking agent is about 31:1 to 40:1. In certain embodiments, the invention relates to an aforementioned method, wherein the ratio (w/w) of activated polyalkylene glycol diacid derivative to crosslinking agent is about 41:1 to 50:1. In certain embodiments, the invention relates to an aforementioned method, wherein the ratio (w/w) of activated polyalkylene glycol diacid derivative to crosslinking agent is about 51:1 to 60:1. In certain embodiments, the invention relates to an aforementioned method, wherein the ratio (w/w) of activated polyalkylene glycol diacid derivative to crosslinking agent is about 61:1 to 70:1.

In certain embodiments, the invention relates to an aforementioned method, further comprising the step of applying a biodegradable polymer to the wound, void, or tissue of a patient; wherein said biodegradable polymer is poly(lactic acid), poly(glycolic acid), or a copolymer thereof.

In certain embodiments, the invention relates to an aforementioned method, further comprising the step of applying a polymer to the wound, void, or tissue of a patient; wherein said polymer is collagen, hyaluronic acid, albumin, cellulose, elastin, fibrin, fibronectin, gelatine, heparin, heparin sulfate, polylysine, poly(vinyl acetate), polyvinylpyrrolidone, poly(acrylic acid), poly(ethylene glycol), poly(propylene glycol)-poly(ethylene glycol) copolymer, trimethylene carbonate, or a polypeptide comprising the tripeptide Arg-Gly-Asp.

In certain embodiments, the invention relates to an aforementioned method, further comprising the step of applying a pre-formed hydrogel to the wound, void, or tissue of a patient; wherein said pre-formed hydrogel is a polyalkyleneimine hydrogel as described herein.

In certain embodiments, the invention relates to an aforementioned method, further comprising the step of applying a dissolvable polymer or inorganic salt to the wound, void, or tissue of a patient. In certain embodiments, the invention relates to an aforementioned method, wherein said dissolvable polymer is formulated as a microsphere or nanosphere.

In certain embodiments, the invention relates to an aforementioned method, further comprising the step of applying a mesh to the wound, void, or tissue of a patient.

In certain embodiments, the invention relates to an aforementioned method, wherein the hydrogel formed has pores in the range from about 1 micron to about 100 microns in diameter.

In certain embodiments, the invention relates to an aforementioned method, wherein the activated polyalkylene glycol diacid derivative and the crosslinking agent are combined in an aqueous solution; and wherein immediately following combination said aqueous solution has an osmolality of 100-700 mOs/kg.

In certain embodiments, the invention relates to an aforementioned method, wherein the area of said wound is less than about 2000 $cm^2$.

In certain embodiments, the invention relates to an aforementioned method, wherein said wound is in the eye. In certain embodiments, the invention relates to an aforementioned method, wherein said wound is in the liver. In certain embodiments, the invention relates to an aforementioned method, wherein said wound is in the lung. In certain embodiments, the invention relates to an aforementioned method, wherein said wound is in the heart. In certain embodiments, the invention relates to an aforementioned method, wherein said wound is the pancreas. In certain embodiments, the invention relates to an aforementioned method, wherein said wound is in the dura matter. In certain embodiments, the invention relates to an aforementioned method, wherein said wound is in an artery or vein. In certain embodiments, the invention relates to an aforementioned method, wherein said wound is in cartilage. In certain embodiments, the invention relates to an aforementioned method, wherein said wound is in a vertebral disk. In certain embodiments, the invention relates to an aforementioned method, wherein said wound is in a sinus cavity. In certain embodiments, the invention relates to an aforementioned method, wherein said wound is in or around the ear. In certain embodiments, the invention relates to an aforementioned method, wherein said wound is of the type classified as a tissue plane. In certain embodiments, the invention relates to an aforementioned method, wherein said wound is associated with a mastectomy. In certain embodiments, the invention relates to an aforementioned method, wherein said wound is in the dura mater of the nervous system. In certain embodiments, the invention relates to an aforementioned method, wherein said wound is in a cardiac artery or cardiac vein.

In certain embodiments, the invention relates to an aforementioned method, further comprising applying a medicament, colorant, flavoring, scent, fibrous additive, thickener or plasticizer.

In certain embodiments, the invention relates to an aforementioned method, wherein said patient is a primate, bovine, equine, feline, or canine. In certain embodiments, the invention relates to an aforementioned method, wherein the patient is a human.

In certain embodiments, the invention relates to an aforementioned method, further comprising the step of sterilizing the activated polyalkylene glycol diacid derivative with e-beam radiation. In certain embodiments, the invention relates to an aforementioned method, further comprising the step of sterilizing the crosslinking agent with e-beam radiation. In certain embodiments, the invention relates to an aforementioned method, wherein said e-beam radiation is between 2 and 40 kGy. In certain embodiments, the invention relates to an aforementioned method, further comprising the step of sterilizing the activated polyalkylene glycol diacid derivative to provide a Sterility Assurance Level (SAL) of at least about $10^{-3}$. In certain embodiments, the invention relates to an aforementioned method, further comprising the step of sterilizing the crosslinking agent to provide a Sterility Assurance Level (SAL) of at least about $10^{-3}$. In certain embodiments, the invention relates to an aforementioned method, further comprising the step of sterilizing the activated polyalkylene glycol diacid derivative to provide a Sterility Assurance Level (SAL) of at least about $10^{-4}$. In certain embodiments, the invention relates to an aforementioned method, further comprising the step of sterilizing the crosslinking agent to provide a Sterility Assurance Level (SAL) of at least about $10^{-4}$. In certain embodiments, the invention relates to an aforementioned method, further comprising the step of sterilizing the activated polyalkylene glycol diacid derivative to provide a Sterility Assurance Level (SAL) of at least about $10^{-5}$. In certain embodiments, the invention relates to an aforementioned method, further comprising the step of sterilizing the crosslinking agent to provide a Sterility Assurance Level (SAL) of at least about $10^{-5}$. In certain embodiments, the invention relates to an aforementioned method, further comprising the step of sterilizing the activated polyalkylene glycol diacid derivative to provide a Sterility Assurance Level (SAL) of at least about $10^{-6}$. In certain embodiments, the invention relates to an aforementioned method, further comprising the step of sterilizing the crosslinking agent to provide a Sterility Assurance Level (SAL) of at least about $10^{-6}$.

In certain embodiments, the invention relates to an aforementioned method, further comprising the step of applying a prosthetic material to the wound, void, or tissue of a patient.

In certain embodiments, the invention relates to an aforementioned method, wherein the prosthetic material is mesh.

In certain embodiments, the invention relates to an aforementioned method, wherein said wound is in the dura mater of the nervous system.

In certain embodiments, the invention relates to an aforementioned composition, wherein R is methyl or H. In certain embodiments, the invention relates to an aforementioned composition, wherein R is H.

In certain embodiments, the invention relates to an aforementioned method, wherein R is methyl or H. In certain embodiments, the invention relates to an aforementioned method, wherein R is H.

In certain embodiments, the invention relates to an aforementioned method, wherein the microbial population comprises bacteria or viruses. In certain embodiments, the invention relates to an aforementioned method, wherein the microbial population comprises bacteria. In certain embodiments, the invention relates to an aforementioned method, wherein the microbial population comprises *S. aureus*. In certain embodiments, the invention relates to an aforementioned method, wherein the microbial population comprises *K. pneumoniae*.

DEFINITIONS

For convenience, certain terms employed in the specification and appended claims are collected here. These definitions should be read in light of the entire disclosure and understood as by a person of skill in the art.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "nucleophile" is recognized in the art, and as used herein means a chemical moiety having a reactive pair of electrons.

The term "electrophile" is art-recognized and refers to chemical moieties which can accept a pair of electrons from a nucleophile as defined above. Electrophilic moieties useful in the method of the present invention include halides and sulfonates.

The term "tissue plane" refers to separated anatomical structures or tissues which allow for the collection of sersanguinous fluid and blood.

The term "polymerize" as used herein refers to the process of converting a monomer to a chain of monomers, wherein the chain of monomers comprises at least about 5 monomers. In certain embodiments, the chain of monomers comprises at least about 10 or 15 monomers. In certain embodiments, the chain of monomers comprises at least about 25 or 40 monomers. In certain embodiments, the chain of monomers comprises at least about 50 or 75 monomers. In certain embodiments, the chain of monomers comprises at least about 100 or 150 monomers. In instances wherein the monomeric unit has more than one functional group capable of forming a bond in the polymerization reaction, the term "polymerize" indicates that at least one of functional groups capable of forming a bond in the polymerization reaction forms a bond with another compound, generally speaking, the other compound is another monomer. In certain embodiments, at least about 10% of the functional groups capable of forming a bond in a polymerization reaction form a bond to another monomer. In certain embodiments, at least about 25% of the functional groups capable of forming a bond in a polymerization reaction form a bond to another monomer. In certain embodiments, at least about 50% of the functional groups capable of forming a bond in a polymerization reaction form a bond to another monomer. In certain embodiments, at least about 75% of the functional groups capable of forming a bond in a polymerization reaction form a bond to another monomer. In certain embodiments, about 20% to about 50% of the functional groups capable of forming a bond in a polymerization reaction form a bond to another monomer.

The term "crosslinker" refers to a moiety or reagent that connects two or more polymers or segments of a polymer. A covalent crosslinker forms a covalent bond to one or more of the polymers or segments of the polymer crosslinked. A polymer that comprises a crosslinker may be said to be a crosslinked polymer.

The term "adhesive" refers to a material that bonds two items to each other, either permanently or temporarily. For example, an adhesive may bond to each other two tissue surfaces.

The term "seal" as used herein indicates that a protective barrier is formed over the wound. In certain embodiments, the protective barrier is a continuous layer. In certain embodiments, the protective barrier is a discontinuous layer, i.e., a layer that has holes or pores in the layer. In certain embodiments, the discontinuous layer comprises less than about 25% holes. In certain embodiments, the discontinuous layer comprises about less than 15% holes. In certain embodiments, the discontinuous layer comprises about less than 5% holes. In the instance where the protective barrier is a continuous layer, in certain embodiments, certain fluids or gases can penetrate through the layer.

For purposes of this invention, the chemical elements are identified in accordance with the Periodic Table of the Elements, CAS version, Handbook of Chemistry and Physics, 67th Ed., 1986-87, inside cover.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, alkylthio, sulfonyl, sulfonamido, ketone, aldehyde, ester, heterocyclyl, aromatic or heteroaromatic moieties, trifluoroalkyl, cyano, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, alkylthio, sulfonyl, ketone, aldehyde, ester, a heterocyclyl, an aromatic or heteroaromatic moiety, trifluoroalkyl, cyano, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, alkylthio, sulfonyl, ketone, aldehyde, ester, a heterocyclyl, an aromatic or heteroaromatic moiety, trifluoroalkyl, cyano, or the like.

The term "carbocycle" is art-recognized and refers to an aromatic or non-aromatic ring in which each atom of the ring is carbon.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2^-$. "Halide" designates the corresponding anion of the halogens, and "pseudohalide" has the definition set forth on page 560 of "Advanced Inorganic Chemistry" by Cotton and Wilkinson, that is, for example, monovalent anionic groups sufficiently electronegative to exhibit a positive Hammett sigma value at least equaling that of a halide (e.g., CN, OCN, SCN, SeCN, TeCN, $N_3$, and $C(CN)_3$).

The terms "amine" and "amino" are art-recognized and refer to both unsubstituted and substituted amines, e.g., a moiety that may be represented by the general formulas:

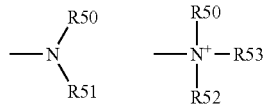

wherein R50, R51, R52 and R53 each independently represent a hydrogen, an alkyl, an alkenyl, —$(CH_2)_m$—R61, or R50 and R51 or R52, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

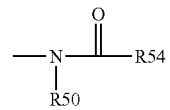

wherein R50 is as defined above, and R54 represents a hydrogen, an alkyl, an alkenyl or —$(CH_2)_m$—R61, where m and R61 are as defined above.

The term "amido" is art recognized as an amino-substituted carbonyl and includes a moiety that may be represented by the general formula:

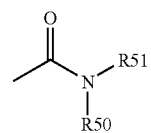

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "carboxyl" is art recognized and includes such moieties as may be represented by the general formulas:

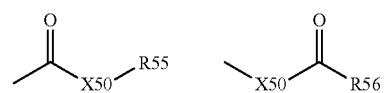

wherein X50 is a bond or represents an oxygen or a sulfur, and R55 and R56 represents a hydrogen, an alkyl, an alkenyl, —$(CH_2)_m$—R61 or a pharmaceutically acceptable salt, R56 represents a hydrogen, an alkyl, an alkenyl or —$(CH_2)_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

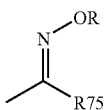

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

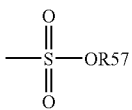

in which R57 is an electron pair, hydrogen, alkyl, cycloalkyl, or aryl.

The term "sulfate" is art recognized and includes a moiety that may be represented by the general formula:

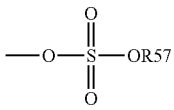

in which R57 is as defined above.

The term "sulfonamido" is art recognized and includes a moiety that may be represented by the general formula:

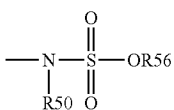

in which R50 and R56 are as defined above.

The term "sulfamoyl" is art-recognized and refers to a moiety that may be represented by the general formula:

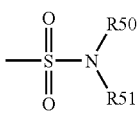

in which R50 and R51 are as defined above.

The term "sulfonyl" is art-recognized and refers to a moiety that may be represented by the general formula:

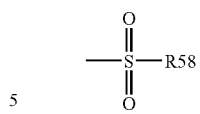

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

in which R58 is defined above.

The term "phosphoryl" is art-recognized and may in general be represented by the formula:

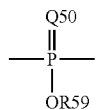

wherein Q50 represents S or O, and R59 represents hydrogen, a lower alkyl or an aryl. When used to substitute, e.g., an alkyl, the phosphoryl group of the phosphorylalkyl may be represented by the general formulas:

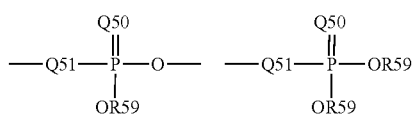

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

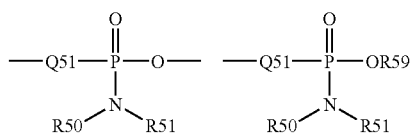

wherein Q51, R50, R51 and R59 are as defined above.

The term "phosphonamidite" is art-recognized and may be represented in the general formulas:

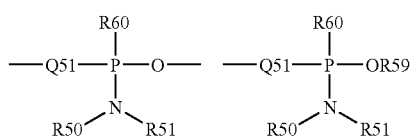

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R61, m and R61 being defined above.

The term "PEG(NHS)$_2$" refers to a polyethylene glycol having the following functional group at both ends of the polymer chain:

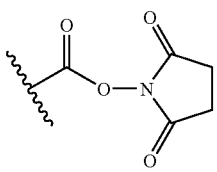 [SMILES: *C(=O)ON1C(=O)CCC1=O]

PEG(NHS)$_2$ can be prepared using either of the following methods. In method 1, a polyethylene glycol is subjected to oxidative conditions in order to oxidize the two termini to the corresponding carboxylic acids [HO$_2$CCH$_2$O-PEG-OCH$_2$CO$_2$H], followed by transformation to the bis(NHS ester). In method 2, PEG(NHS)$_2$ is prepared by alkylation of the two termini of a polyethylene glycol with acrylonitrile to give NCCH$_2$CH$_2$O-PEG-OCH$_2$CH$_2$CN, followed by hydrolysis to the bis(acid) [HO$_2$CCH$_2$CH$_2$O-PEG-OCH$_2$CH$_2$CO$_2$H], and then transformation to the bis(NHS ester).

The term "SS" refers to the following chemical group:

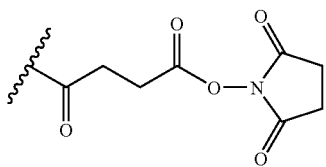 [SMILES: *C(=O)CCC(=O)ON1C(=O)CCC1=O]

The term "SG" refers to the following chemical group:

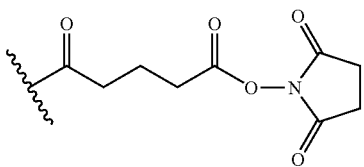 [SMILES: *C(=O)CCCC(=O)ON1C(=O)CCC1=O]

The term "SA" refers to the following chemical group:

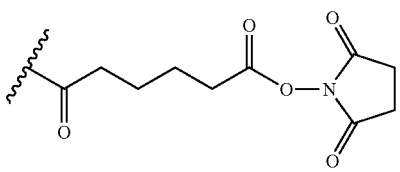 [SMILES: *C(=O)CCCCC(=O)ON1C(=O)CCC1=O]

The term "SSub" refers to the following chemical group:

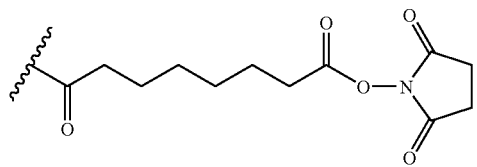 [SMILES: *C(=O)CCCCCCC(=O)ON1C(=O)CCC1=O]

The term "SSeb" refers to the following chemical group:

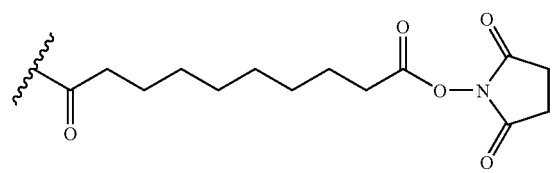 [SMILES: *C(=O)CCCCCCCCC(=O)ON1C(=O)CCC1=O]

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The definition of each expression, e.g., alkyl, m, n, and the like, when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2 ed.; Wiley: New York, 1991). Protected forms of the inventive compounds are included within the scope of this invention.

While several embodiments of the present invention are described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

EXEMPLIFICATION

The invention now being generally described, it will be more readily understood by reference to the following examples which are included merely for purposes of illustration of certain aspects and embodiments of the present invention, and are not intended to limit the invention.

Example 1

Synthesis of Difunctional N-hydroxysuccinimide Activated PEGs from Difunctional PEG-OH Via Anhydrides A general synthetic process is as follows, the detailed list of various PEGs, linkages, and amounts of various reagents are listed in the table. In general, difunctional PEG-OH was added to a 3-neck, dry round bottom flask affixed with a nitrogen/vacuum line, heating apparatus and stirring mechanism. While being stirred, the flask was heated to ~120° C. until all PEG had melted. The flask was then allowed to stir for 30 minutes under high vacuum, with the temperature being lowered to ~80° C. for the duration of the reaction. Prior to any subsequent reagent addition, the flask was purged three times with nitrogen. To the flask, a catalytic amount of a diacid acid was added and allowed to dissolve. Next, an excess of the diacid anhydride was added to the flask and the system was put under nitrogen. The reaction was allowed to stir under nitrogen at 80° C. for a minimum of 18 hours. The flask was then cooled and the content dissolved in a minimum amount of dichloromethane (DCM). This solution was slowly added to approximately five times that volume of diethyl ether while stirring at room temperature. Using vacuum filtration, the precipitate was isolated and rinsed with a minimum of diethyl ether. The precipitate was then transferred to a round bottom flask and allowed to dry under high vacuum. The derivatized PEG was transferred to a 3-neck, dry round bottom flask and affixed with a nitrogen line, chilling apparatus, liquid addition apparatus and stirring mechanism. While stirring under nitrogen, an amount of dichloromethane equal to twice the amount of derivatized PEG was added. The appropriate excess of N-hydroxysuccinimide was then added and allowed to stir at room temperature for a minimum of 30 minutes. The flask was cooled to −2.5-2.5° C. An approximate 1 M solution of N,N'-dicyclohexylcarbodiimide (DCC) was then added via syringe pump over 6 hours to the cooled flask. The reaction was allowed to stir for an additional 18 hours while still under nitrogen at approximately 0° C. The insoluble N,N'-dicyclohexylurea (DCU) was filtered and rinsed with a minimum of DCM using vacuum filtration. The resulting solution was then concentrated before a volume of diethyl ether approximately five times the volume of the concentrate was slowly added while stirring at room temperature. The precipitate was filtered and rinsed with a minimum of diethyl ether using vacuum filtration. While still wet with ether, the precipitate was then added to a Soxhlet extractor thimble and extracted with diethyl ether for 72 hours. The precipitate was then transferred to a round bottom flask and allowed to dry under vacuum. See FIG. 8A.

Example 2

Synthesis of Difunctional N-hydroxysuccinimide Activated PEGs from Difunctional PEG-OH Via Diacids A general synthetic process is as follows, the detailed list of various PEGs, linkages, and amounts of various reagents are listed in the table. In general, difunctional PEG-OH was added to a 3-neck, dry round bottom flask affixed with a Dean-Stark apparatus/reflux condenser, heating apparatus, and stirring mechanism. While stirring under nitrogen, an amount of toluene equal to seven times the amount of derivatized PEG was added. To the flask, an excess of the diacid was added followed by a catalytic amount of 50 wt % sulfuric acid and the system was put under nitrogen. The reaction was allowed to stir at reflux for a minimum of 5 hours. The flask was then cooled, the toluene was removed under reduced pressure, and the remaining contents were dissolved in an amount of dichloromethane (DCM) equal to twice the amount of PEG. This solution was slowly added to approximately five times that volume of diethyl ether while stirring at room temperature. Using vacuum filtration, the precipitate was isolated and rinsed with a minimum of diethyl ether. The precipitate was then transferred to a round bottom flask and allowed to dry under high vacuum. The derivatized PEG was transferred to a 3-neck, dry round bottom flask and affixed with a nitrogen line, chilling apparatus, liquid addition apparatus and stirring mechanism. While stirring under nitrogen, an amount of dichloromethane equal to twice the amount of derivatized PEG was added. The appropriate excess of N-hydroxysuccinimide was then added and allowed to stir at room temperature for a minimum of 30 minutes. The flask was cooled to −2.5-2.5° C. An approximate 1M solution of N,N'-dicyclohexylcarbodiimide (DCC) was then added via syringe pump over 6 hours to the cooled flask. The reaction was allowed to stir for an additional 18 hours while still under nitrogen at approximately 0° C. The insoluble N,N'-dicyclohexylurea (DCU) was filtered and rinsed with a minimum of DCM using vacuum filtration. The resulting solution was then concentrated before a volume of diethyl ether approximately five times the volume of the concentrate was slowly added while stirring at room temperature. The precipitate was filtered and rinsed with a minimum of diethyl ether using vacuum filtration. While still wet with ether, the precipitate was then added to a Soxhlet extractor thimble and extracted with diethyl ether for 72 hours. The precipitate was then transferred to a round bottom flask and allowed to dry under vacuum. See FIG. 8B.

Example 3

Summary of Various Polyalkyleneimine (PAI)/Polyalkyleneglycol (PAG) Hydrogel Formulation Composition The following table lists the activated PAG and either polyalkyleneimine or trilysine combinations that that were used to make various hydrogels for analysis. All of the following gels were prepared by creating one polyalkyleneimine and one trilysine crosslinking agent solution and mixing the solutions at the appropriate ratio or concentration of components with the list of activated polyalkylene glycols. The table lists the composition and molecular weight of the PAI and activated PAG, the weight percent of PAI and activated PAG used in the formulation, the weight ratio of PAG:PAI, the swelling at 24 hours in PBS pH 6.0 at 37° C., the set time of the formulation, and the amounts of various components used to achieve the reported set time. See FIG. 9 for a chart comparing the swelling of the formulations in 24 hours in PBS pH 7.4 at 37° C.

Example 4

Antimicrobial Assays

Gram Positive and Gram Negative Bacteria

A study was done in order to determine the antimicrobial properties of formulation 1 and formulation 3, following a modified version of AATCC Test Method 100. The identities of formulation 1 and formulation 3 are as follows:
Formulation 1 is a 15 wt % hydrogel formulation based on a PEG Mw=3400 (PEG Mw=3350) succinimidyl sebacate and PEI Mw=2000. The PEG and PEI are typically dissolved in separate phosphate and/or borate buffers at time of use. The stoichiometry of the PEG and PEI components was adjusted to provide a PEG activated ester to PEI primary amine ratio of 1.15:1.
Formulation 3 is a 15 wt % hydrogel formulation based on a PEG Mw=3400 (PEG Mw=3350) succinimidyl sebacate and PEI Mw=2000. The PEG and PEI are typically dissolved in separate phosphate and/or borate buffers at time of use. The stoichiometry of the PEG and PEI components were adjusted to provide a PEG activated ester to PEI primary amine ratio of 0.5:1.

In order to test a gram negative and a gram positive organism after 24-hour exposure to the hydrogel materials, two samples of formulation 1 and two samples of formulation 3 were prepared in the sanitized laminar flow hood. The samples were prepared in 48-mm discs. The inoculum carrier was nutrient broth and the neutralizer was letheen broth.

The hydrogel samples were tested with a known quantity of each organism and the data is presented in FIG. 10. Formulation 1 showed no reduction (NR) for *S. aureus* (a gram positive bacteria) and 74.35% reduction for *K. pneumoniae* (a gram negative bacteria). Formulation 3 showed >99.95% reduction for *S. aureus* (a gram positive bacteria) and >99.85% reduction for *K. pneumoniae* (a gram negative bacteria).

In a second experiment, one sample of each material was prepared instead of two samples, as explained above. The time zero samples were not performed in this experiment, and time zero was assumed to be the counted number of organisms.

Both formulation 1 and formulation 3 exhibited antimicrobial properties. Formulation 1 did not promote or inhibit the growth of *S. aureus* and significantly reduced the concentration of *K. pneumoniae*. Formulation 3 dramatically reduced the concentration of both *S. aureus* and *K. pneumoniae*.

Example 5

Antimicrobial Assays

Variation of R Value and PEG End-Group Modification

A study was done in order to further investigate the antimicrobial properties of formulation 1 and formulation 3, and to determine the antimicrobial properties of formulation 2 and formulation 4. The composition of formulation 1 and formulation 3 were described in Example 4. The identities of formulation 2 and formulation 4 are as follows:
Formulation 2 is a 15 wt % hydrogel formulation based on a bifunctional polyethylene glycol (PEG) Mw=3400 (PEG Mw=3350) succinimidyl sebacate and a polyfunctional polyethyleneimine Mw=2000 (PEI). The stoichiometry of the PEG and PEI components was adjusted to provide a PEG activated ester to PEI primary amine ratio of 0.75:1.
Formulation 4 is a 15 wt % hydrogel formulation based on a bifunctional polyethylene glycol (PEG) Mw=3400 (PEG Mw=3350) succinimidyl glutarate and a polyfunctional polyethyleneimine Mw=2000 (PEI). The stoichiometry of the PEG and PEI components was adjusted to provide a PEG activated ester to PEI primary amine ratio of 0.75:1.

To confirm the results of the Example 4, and to further explore the proper components and ratios necessary to confer anti-microbial activity, 50 mm diameter films of formulation 1, a formulation 2, formulation 3, and formulation 4 were prepared in the sanitized laminar flow hood. AATCC Test Method 100 was used, as previously.

Formulations 1, 2, and 3 all contain the same $PEG_{3350}$-SSeb and $PEI_{2000}$, they are all 15 weight percent hydrogels, and they are all buffered to set in approximately 1 second. The only difference between formulations 1, 2, and 3 is the PEG active ester to PEI primary amine ratio (R value) and the final extract pH of the formulation. This information is depicted in FIG. 11.

Formulation 4 also forms a 15 weight percent hydrogel and has a PEG active ester to PEI primary amine ratio (R value) of 0.75—the same ratio as Formulation 2. Formulation 4 is different in that the PEG diacid composition is switched to glutaric acid, so the two active components are $PEG_{3350}$-SG and $PEI_{2000}$ which, when mixed, have been buffered to set in approximately 30-45 seconds. Due to the slower set time the extract pH of formulation 4 is also lower—6.54 pH.

The extract pHs reported here should not affect the overall survival of the bacteria on test. If anything were to be affected, the lower pH extracts may begin to limit growth of bacteria since the bacteria excrete acidic waste, lowering the pH further.

Formulation 1 showed no reduction (NR) for *S. aureus* (a gram positive bacteria) (n=3). These results are depicted in FIG. 12.

Formulation 2 showed >99.93% reduction for *S. aureus* (a gram positive bacteria) (n=3). These results are depicted in FIG. 13.

Formulation 3 showed >99.93% reduction for *S. aureus* (a gram positive bacteria) (n=3). These results are depicted in FIG. 14.

Formulation 4 showed no reduction (NR) for *S. aureus* (a gram positive bacteria) (n=2). Further, formulation 4 showed no reduction (NR) for *K. pneumoniae* (a gram negative bacteria) (n=2). These results are depicted in FIG. 15.

In summary, formulation 1 appeared not to inhibit the growth of *S. aureus* during a triplicate re-test. Both formulation 2 and formulation 3 exhibited substantial antimicrobial properties against *S. aureus*. Formulation 4 appeared not to inhibit the growth of *S. aureus* or *K. pneumoniae* during a duplicate test of each organism.

Example 6

In Vivo Studies

Formulation 1 as a Dural Sealant

Formulation 1, as described above, was tested as a dural sealant in dogs. Typically, the formulation is mixed and applied (1:1 ratio of PEI solution to PEG solution) through an applicator. It sets within approximately 1 second.

Formulation 1 was applied to a sutured durotomy site in eight (n=8) dogs. In seven (n=7) dogs, the durotomy site was closed with sutures only. The suture-only dogs served as control animals. At seven days post-surgery, three (n=3) dogs that received the test article and three (n=3) dogs serving as controls were sacrificed. The remaining five (n=5) test article animals and four (n=4) control animals were sacrificed at 170 or 172 days post-surgery. The animals were assigned to the treatment groups as illustrated in FIG. 17.

Under inhalant anesthesia, a midline cranial incision was made and the animals had an approximate 3-cm×2-cm bone flap removed using a 1.4-mm burr drill bit. An approximate 2-cm incision was made through the dura and the arachnoid so that cerebrospinal fluid (CSF) was allowed to freely egress, leaving a gap of approximately 2 mm. Once the 2-cm incision was made and CSF leakage verified, the dura was loosely approximated with 6-0 nylon suture. In the treated animals, the incision was blotted dry and the test article was applied to a depth of approximately 1.0 mm. Once the test article had significantly cured, the durotomy site was tested for CSF leakage with a Valsalva maneuver up to 20 cm $H_2O$. The test article was allowed to cure and the bone flap was replaced, held in place with 2-0 nylon sutures and dental acrylic. In the control animals, CSF leakage was verified by a Valsalva maneuver up to 20 cm $H_2O$ (no test article was applied); the bone flap was replaced and held in place with 2-0 nylon sutures and dental acrylic.

Animals were subjected to MRI examination at 2 to 3 days following surgery and monthly thereafter to assess the degradation profile (change in area over time) of Formulation 1 and for any morphologic changes that may have occurred.

The effectiveness of formulation 1 was evaluated at Day 8 (i.e., 7 days post-surgery) in the first series of animals sacrificed. The next series of animals was evaluated at 6 months (i.e., 170 or 172 days post-surgery) in seven (n=7, 4 treatment, 3 control) animals at the long-term follow-up time-point. In the 6-month follow-up series, the safety and endurance of formulation 1 was evaluated using serial magnetic resonance imaging (MRI) to assess the material degradation profile as well as any morphologic changes associated with the sealant. Multiple MRI sequences were used, including T2 weighted coronal, T1 coronal (+contrast) and fluid attenuated inversion recovery (FLAIR). These long-term animals also underwent pressure testing and clinical pathology at 6-month follow-up. Two additional animals (n=2, 1 treatment, 1 control) were sacrificed at 6-month follow-up for histopathology purposes only. Histopathology was performed in all 15 animals.

The results for the study indicated that there were no test article-related changes related to food consumption or body weight, nor were there any changes in neurological/physical examinations or clinical pathology parameters for any animal during the course of the study.

The hydrogel was tough and flexible and did not allow CSF to leak at pressures up to 68 cm $H_2O$. A summary of the pressure data obtained on Day 8 is presented in FIG. 18.

The formulation 1-treated group had higher initial ICP and maximum ICP compared to control animals. Additionally, the formulation 1-treated animals had no signs of CSF leakage at the dural incision at baseline, however all of the control animals exhibited CSF leakage at baseline. Animals in the formulation 1-treated group did not have evidence of peridural adhesions; however peridural adhesions were noted in all animals in the control group. Histopathological evaluations at Day 8 indicated that the single topical administration of formulation 1 to a durotomy site in dogs was not associated with any adverse morphologic changes. Based on the histopathology, there were not sufficient differences to indicate a distinct effect (positive or negative) of the test article on healing the durotomy site. Test article was visible at the durotomy site in the animals examined seven days after surgery.

At six months, the hydrogel was not present macroscopically. The intracranial pressure (ICP) was measured using the ICP transducer. A summary of the pressure data obtained at 6 months is presented in FIG. 19.

The formulation 1-treated group had higher initial ICP and maximum ICP compared to control animals. Additionally, the formulation 1-treated animals had no signs of CSF leakage at the dural incision at baseline, however two of the three control animals exhibited CSF leakage at baseline. One of the control animals exhibited strong adhesions between the dura and the bone flap, making it impossible to determine whether the wound was leaking spontaneously or as a result of dural tearing during bone flap removal.

Histopathological evaluations at Day 170-172 indicated that the single topical administration of formulation 1 to a durotomy site in dogs was not associated with any adverse morphologic changes. The test article was no longer visible at the durotomy site in the animals examined six months after surgery. Any flattening of the cerebral cortical tissue underlying the site of test article application was not associated with any microscopic changes and was completely resolved in the brains from animals examined on Days 170 to 172. This slight displacement of the cerebral cortical tissue was not considered to be an adverse effect. There were no adverse changes in the brain, calvarium, dura, meninges, or non-nervous system organs associated with the test article. All changes in those tissues were considered to be associated with the surgery or to be incidental and of no biologic significance.

A review of the MRI scans shows the test material clearly visible at 2-3, 30, and 60 days following surgery. However, it is not readily discernable at day 90 post-surgery. The degradation of the sealant can be followed most clearly in the T2 images (hyperintense becoming isointense signal on T-2 due to increasing amount of free water in the hydrogel). By monitoring the T2 images over time, it appears the area of the hydrogel decreased approximately 50% at the 1 month scan. This degradation continued through the 2- and 3-month scans and the test material is barely discernable in the 4-month T2 images. The test material is not discernable in the 5- and 6-month T2 images.

It can be concluded that the use of formulation 1 is effective in preventing cerebrospinal fluid leaks when applied as an adjunct to sutures in the canine durotomy model. Intracranial pressure (ICP) testing in the treated animals at the 1-week necropsy and the 6-month necropsy both showed prevention of CSF leakage when challenged with superphysiologic intracranial pressures. In contrast, 4/6 control animals were leaking at baseline and 1/6 was leaking due to a tear in the dura.

Example 7

In Vivo Studies

Hernia Mesh Fixation by Formulations 3, 4, and 5

Formulations 3 and 4 were described previously. Formulation 3 is typically mixed (1:1 ratio of PEI solution to PEG solution) and applied through an applicator, setting in approximately 1 second. Formulation 4 is typically mixed and applied through a brush applicator, setting in approximately 30 seconds (set time was adjusted with phosphate and borate buffers).

Formulation 5 is a 10 wt % hydrogel formulation based on a PEG Mw=10000 succinimidyl sebacate and PEI Mw=2000. The PEG and PEI are typically dissolved in separate phosphate and/or borate buffers at time of use. The stoichiometry of the PEG and PEI components were adjusted to provide a PEG activated ester to PEI primary amine ratio of 1.05:1. The formulation is typically mixed and applied (1:1 ratio of solutions) through an applicator, setting in approximately 1 second.

Figure 20:
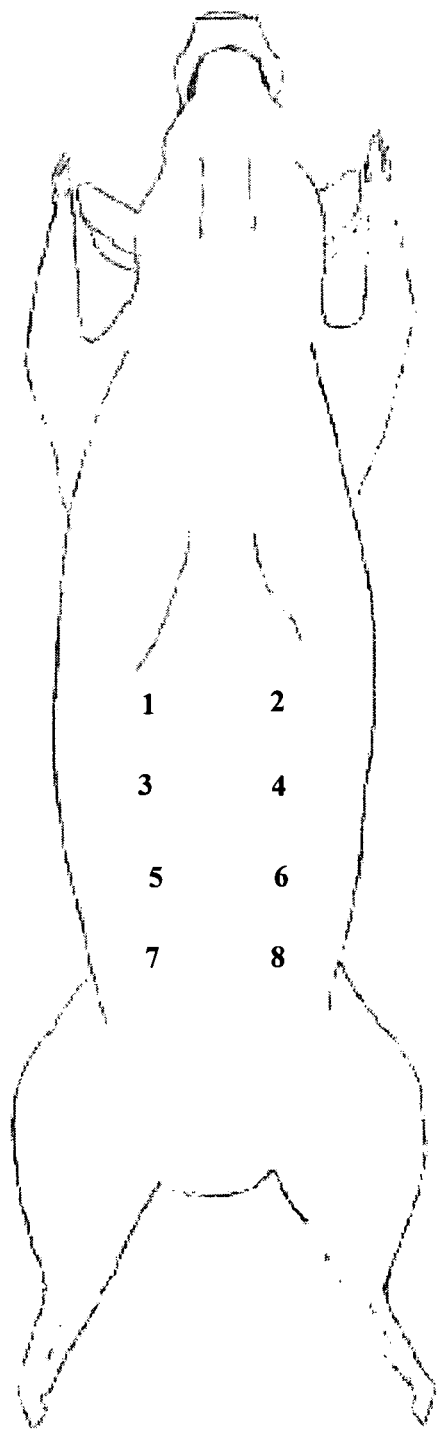
FIG. 20 depicts the location of the implanted soft mesh hernia patches in each animal in the study of the mesh fixation properties of formulations 3, 4, and 5.

Four animals were anesthetized and prepped for surgery. A ventral midline incision was made to provide access to the abdominal cavity. In each animal, 8 Bard Soft Mesh hernia patches (1.5 inch×1.5 inch square) were implanted intra-abdominally against the peritoneal wall in contact with the viscera in the locations indicated in FIG. 20.

The meshes were implanted in a linear fashion 2-3 cm from the linea alba and 2-3 cm apart from each other. On the right side of the intraabdominal wall, 4 patches were placed linearly (in random order) representing the 4 treatment groups: mesh adhered using formulation 3, mesh adhered using formulation 4, mesh adhered using formulation 5, and mesh adhered using Endopath EMS 5 mm titanium staples (positive control). The same procedure was repeated on each animal's left intraabdominal wall, resulting in 2 replicates of the 4 treatments per animal. The order of application for each pig was randomized so that every pig received a specific sample type in each of the four superior to inferior positions with the replicate sample placed in the same position on the other side of the animal.

The linea alba and body wall was closed with #3 Vicryl suture in a near-far, far-near pattern. Subcutaneous tissue and skin was closed with 2-0 PDS in a running pattern with buried knots. At day 7 and again at day 21 post-operatively, 2 of the pigs were euthanized. Following euthanasia, tissue from each treatment site was assessed for adhesion formation and patch migration. The sample sites were grossly assessed for adhesion formation and migration of the patch by a general surgeon. All sites samples were graded on extent of adhesions (0-4 scale) and the tenacity of the adhesions (1-3 scale). In general, the first two sites were placed above the liver resulting in full tenacious adhesions in almost all cases. Sites five through eight were considered the best sites for adhesion extent and tenacity. During this study, there were no significant differences in the strength of adhesion formation between the different fixation methods.

Regarding the presence of hydrogel, at day 7, formulation 3 and the control appeared to have significant ingrowth of peritoneum. Hydrogel appeared to be present at day 7 for formulation 3. There appeared to be little ingrowth with formulation 4, although the hydrogel had completely degraded. And, formulation 5 had hydrogel present but little ingrowth was evident, at least macroscopically. Histologically there were no statistical differences in ingrowth. At day 21, Formulation 4 and 5 appeared to be completely degraded and formulation 3 had significantly degraded.

Following patch migration, and extent and tenacity grading, the implant sites were evaluated histologically and mechanically.

Mesh implants on one side of the pig were separated into their four sites, sectioned and stained for histological analysis. The pathologist was blinded to the treatments. Each section was graded in each of 4 categories: granulomatous inflammation, suppurative inflammation, fibrosis, and covering. Granulomatous and suppurative inflammation were graded from 0-3: 0=none, 1=mild, 2=moderate, and 3=severe. Fibrosis was graded from 0-3: 0=none, 1=poorly collagenized, 2=collagenized, 3=penetrating through original stroma. Covering was graded from 0-3: 0=no covering, 1=thin, smooth covering, 2=moderately thick covering, 3=thick covering with adhesion. At the three week necropsy interval, formulation 5 and formulation 3 did demonstrate a significant enhanced level of cellular ingrowth compared to the other fixation groups. Further statistical tests revealed mesh location/treatment location had an effect but did not overshadow the differences detected for fibrosis. This increase in ingrowth was remarkable considering polypropylene meshes were already known to incorporate strongly into the host tissue. Otherwise, there were no other significant differences in the formation of fibrosis between the different fixation methods. Further, there were no significant differences in the granulomatous and suppurative inflammation or the amount of covering between the different fixation methods.

For each pig euthanized, a second sample from each of the four groups was harvested for pull-out testing. The maximum load before the hernia mesh to tissue interface was disrupted was noted as well as the crosshead displacement in mm. Mechanical testing of the four different mesh fixation groups did not demonstrate any significant differences in pull-out strength at one or three weeks nor did mesh/treatment location exhibit any effect on the statistical model. These observations demonstrate that atraumatic hydrogel fixation demonstrated similar pull-out strength when compared to conventional fixation.

In conclusion, the hydrogel formulations served effectively as a mesh fixation devices. Of the three formulations tested, formulation 3 was the most effective hydrogel for this particular application. Formulation 3 was the only hydrogel formulation that fixated hernia mesh and prevented all mesh migration and roll-ups. Formulation 3 and formulation 5 were also the only formulations that demonstrated a significant enhancement in the level of cellular ingrowth between the different fixation groups. However, a formulation 5-treated mesh at three weeks did partially roll, and another mesh at one week became dislodged before mechanical testing. Like the other hydrogel formulations, formulation 3 had similar pull-out strength and adhesion formation when compared to conventional fixation.

Prophetic Examples

A. The role of the diacid on the PEG derivative, and whether chain-length of the diacid moiety imparts some antimicrobial properties on the hydrogel, will be examined.
B. The antimicrobial nature of the hydrogels against other bacteria and fungi will be investigated, with a significant number of samples. Additionally, up to a $10^6$ population of inoculum is warranted.
C. The possibility of coating medical devices with the antimicrobial hydrogels will be investigated.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A polymeric composition, comprising an activated polyethylene glycol diacid derivative, and a covalent crosslinking agent; wherein the covalent crosslinking agent is polyethyleneimine having a weight average molecular weight of about 400 to about 2000 Daltons; the molar ratio of activated esters on the polyethylene glycol diacid derivative to primary amines on the polyethyleneimine is within a range of about 0.5:1 to about 1.5:1; and the activated polyethylene glycol diacid derivative is represented by formula I:

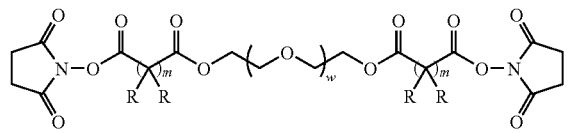

wherein, independently for each occurrence,
R is H; m is 5-10 inclusive; and w is 20 to 120 inclusive.

2. The polymeric composition of claim 1, wherein the polyethyleneimine has a weight average molecular weight of about 2000 Daltons.
3. The polymeric composition of claim 1, wherein m is 8.
4. The polymeric composition of claim 1, wherein the activated polyethylene glycol diacid derivative is $PEG_n$-$(SSeb)_2$; wherein PEG is polyethylene glycol; n represents the number average molecular weight of the PEG; n is about 3350; and SSeb is

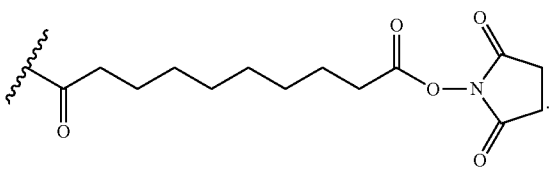 [SMILES: *C(=O)CCCCCCCCC(=O)ON1C(=O)CCC1=O ; "."]

5. The polymeric composition of claim 1, wherein the polymeric composition comprises about 15 weight percent of the polyethylene glycol diacid derivative and the polyethyleneimine.
6. The polymeric composition of claim 1, wherein the molar ratio of activated esters on the polyethylene glycol diacid derivative to primary amines on the crosslinking agent is in the range from about 0.75:1 to about 1.3:1.
7. The polymeric composition of claim 1, wherein the molar ratio of activated esters on the polyethylene glycol diacid derivative to primary amines on the polyethyleneimine is about 0.5:1.
8. The polymeric composition of claim 1, wherein the molar ratio of activated esters on the polyethylene glycol diacid derivative to primary amines on the polyethyleneimine is about 0.75:1.
9. The polymeric composition of claim 1, wherein the molar ratio of activated esters on the polyethylene glycol diacid derivative to primary amines on the polyethyleneimine is about 1.15:1.
10. The polymeric composition of claim 1, wherein the polyethyleneimine has a weight average molecular weight of about 2000 Daltons; and m is 8.
11. The polymeric composition of claim 1, wherein the polyethyleneimine has a weight average molecular weight of about 2000 Daltons; the activated polyethylene glycol diacid derivative is $PEG_n$-$(SSeb)_2$; wherein PEG is polyethylene glycol; n represents the number average molecular weight of the PEG; n is about 3350; and SSeb is

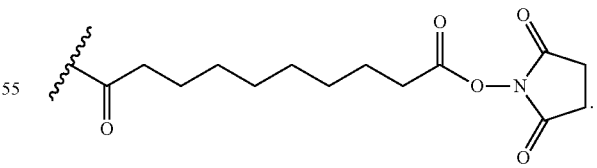

12. The polymeric composition of claim 1, wherein the polyethyleneimine has a weight average molecular weight of about 2000 Daltons; and the polymeric composition comprises about 15 weight percent of the polyethylene glycol diacid derivative and the polyethyleneimine.
13. The polymeric composition of claim 1, wherein the polyethyleneimine has a weight average molecular weight of about 2000 Daltons; and the molar ratio of activated esters on the polyethylene glycol diacid derivative to primary amines on the crosslinking agent is in the range from about 0.75:1 to about 1.3:1.

14. The polymeric composition of claim 1, wherein the polyethyleneimine has a weight average molecular weight of about 2000 Daltons; m is 8; and the polymeric composition comprises about 15 weight percent of the polyethylene glycol diacid derivative and the polyethyleneimine.

15. The polymeric composition of claim 1, wherein the polyethyleneimine has a weight average molecular weight of about 2000 Daltons; m is 8; and the molar ratio of activated esters on the polyethylene glycol diacid derivative to primary amines on the crosslinking agent is in the range from about 0.75:1 to about 1.3:1.

16. The polymeric composition of claim 1, wherein the polyethyleneimine has a weight average molecular weight of about 2000 Daltons; m is 8; the polymeric composition comprises about 15 weight percent of the polyethylene glycol diacid derivative and the polyethyleneimine; and the molar ratio of activated esters on the polyethylene glycol diacid derivative to primary amines on the crosslinking agent is in the range from about 0.75:1 to about 1.3:1.

17. The polymeric composition of claim 1, wherein the polyethyleneimine has a weight average molecular weight of about 2000 Daltons; the activated polyethylene glycol diacid derivative is $PEG_n$-$(SSeb)_2$; wherein PEG is polyethylene glycol; n represents the number average molecular weight of the PEG; n is about 3350; SSeb is

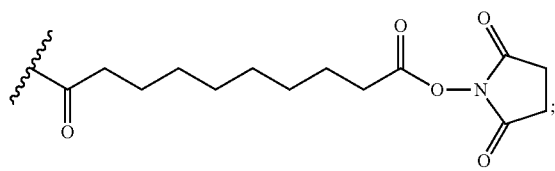 [SMILES: *C(=O)CCCCCCCCC(=O)ON1C(=O)CCC1=O]

and the polymeric composition comprises about 15 weight percent of the polyethylene glycol diacid derivative and the polyethyleneimine.

18. The polymeric composition of claim 1, wherein the polyethyleneimine has a weight average molecular weight of about 2000 Daltons; the activated polyethylene glycol diacid derivative is $PEG_n$-$(SSeb)_2$; wherein PEG is polyethylene glycol; n represents the number average molecular weight of the PEG; n is about 3350; SSeb is

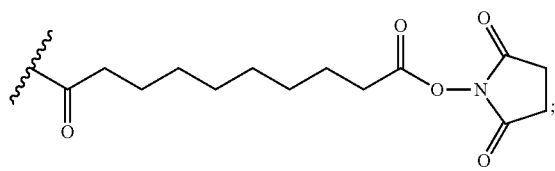 [SMILES: *C(=O)CCCCCCCCC(=O)ON1C(=O)CCC1=O]

and the molar ratio of activated esters on the polyethylene glycol diacid derivative to primary amines on the crosslinking agent is in the range from about 0.75:1 to about 1.3:1.

19. The polymeric composition of claim 1, wherein the polyethyleneimine has a weight average molecular weight of about 2000 Daltons; the activated polyethylene glycol diacid derivative is $PEG_n$-$(SSeb)_2$; wherein PEG is polyethylene glycol; n represents the number average molecular weight of the PEG; n is about 3350; SSeb is

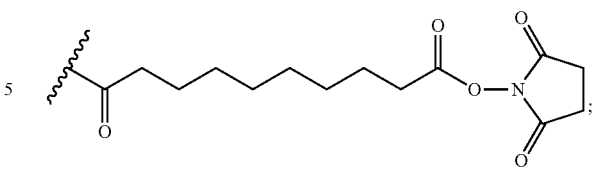

the polymeric composition comprises about 15 weight percent of the polyethylene glycol diacid derivative and the polyethyleneimine; and the molar ratio of activated esters on the polyethylene glycol diacid derivative to primary amines on the crosslinking agent is in the range from about 0.75:1 to about 1.3:1.

20. The polymeric composition of claim 1, wherein the polyethyleneimine has a weight average molecular weight of about 2000 Daltons; the activated polyethylene glycol diacid derivative is $PEG_n$-$(SSeb)_2$; wherein PEG is polyethylene glycol; n represents the number average molecular weight of the PEG; n is about 3350; SSeb is

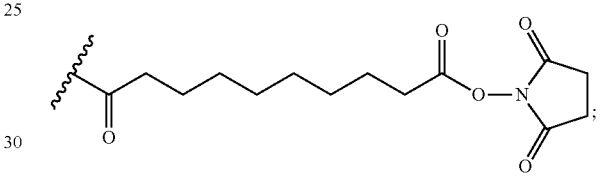

the polymeric composition comprises about 15 weight percent of the polyethylene glycol diacid derivative and the polyethyleneimine; and the molar ratio of activated esters on the polyethylene glycol diacid derivative to primary amines on the polyethyleneimine is about 0.5:1.

21. The polymeric composition of claim 1, wherein the polyethyleneimine has a weight average molecular weight of about 2000 Daltons; the activated polyethylene glycol diacid derivative is $PEG_n$-$(SSeb)_2$; wherein PEG is polyethylene glycol; n represents the number average molecular weight of the PEG; n is about 3350; SSeb is

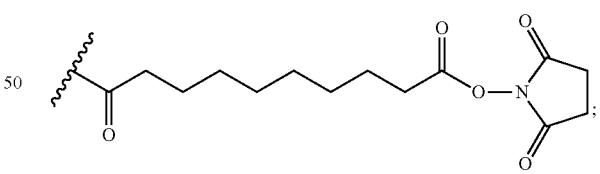

the polymeric composition comprises about 15 weight percent of the polyethylene glycol diacid derivative and the polyethyleneimine; and the molar ratio of activated esters on the polyethylene glycol diacid derivative to primary amines on the polyethyleneimine is about 0.75:1.

22. The polymeric composition of claim 1, wherein the polyethyleneimine has a weight average molecular weight of about 2000 Daltons; the activated polyethylene glycol diacid derivative is $PEG_n$-$(SSeb)_2$; wherein PEG is polyethylene glycol; n represents the number average molecular weight of the PEG; n is about 3350; SSeb is

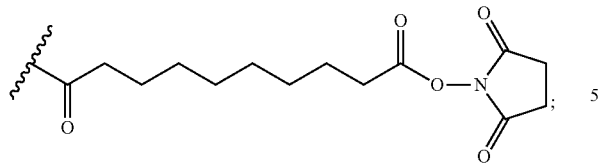; 
the polymeric composition comprises about 15 weight percent of the polyethylene glycol diacid derivative and the polyethyleneimine; and the molar ratio of activated esters on the polyethylene glycol diacid derivative to primary amines on the polyethyleneimine is about 1.15:1.
* * * * *